US012780917B2

(12) United States Patent
Nakano et al.

(10) Patent No.: US 12,780,917 B2
(45) Date of Patent: Nov. 3, 2026

(54) ANTI-CADM1 ANTIBODY

(71) Applicants: The University of Tokyo, Tokyo (JP); University of the Ryukyus, Okinawa (JP)

(72) Inventors: Kazumi Nakano, Tokyo (JP); Toshiki Watanabe, Yokohama (JP); Kouhei Tsumoto, Tokyo (JP); Aki Tanabe, Tokyo (JP); Yoshiaki Takahashi, Okinawa (JP)

(73) Assignees: THE UNIVERSITY OF TOKYO, Tokyo (JP); UNIVERSITY OF THE RYUKYUS, Okinawa (JP)

( * ) Notice: Subject to any disclaimer, the term of this patent is extended or adjusted under 35 U.S.C. 154(b) by 469 days.

(21) Appl. No.: 18/289,965

(22) PCT Filed: May 10, 2022

(86) PCT No.: PCT/JP2022/019787

§ 371 (c)(1),
(2) Date: Nov. 8, 2023

(87) PCT Pub. No.: WO2022/239766

PCT Pub. Date: Nov. 17, 2022

(65) Prior Publication Data

US 2024/0317853 A1 Sep. 26, 2024

(30) Foreign Application Priority Data

May 11, 2021 (JP) ................................ 2021-080133

(51) Int. Cl.
*C07K 16/28* (2006.01)
*A61P 35/02* (2006.01)

(52) U.S. Cl.
CPC .......... *C07K 16/2803* (2013.01); *A61P 35/02* (2018.01); *C07K 2317/21* (2013.01); *C07K 2317/24* (2013.01); *C07K 2317/565* (2013.01); *C07K 2317/732* (2013.01); *C07K 2317/77* (2013.01)

(58) Field of Classification Search
None
See application file for complete search history.

(56) References Cited

U.S. PATENT DOCUMENTS

2012/0093826 A1 4/2012 Terrett et al.

FOREIGN PATENT DOCUMENTS

| | | |
|---|---|---|
| JP | 2012-519492 | 8/2012 |
| JP | 2015-007030 | 1/2015 |
| WO | 2010/102175 | 9/2010 |

OTHER PUBLICATIONS

Kuramochi et al., "TSLC1 is a tumor-suppressor gene in human non-small-cell lung cancer," *Nat. Genet.*, 27, 2001, pp. 427-430.
Sasaki et al., "Overexpression of a cell adhesion molecule, TSLC1, as a possible molecular marker for acute-type adult T-cell leukemia," *Blood*, 105, 2005, pp. 1204-1213.
Nakahata et al., "Clinical Significance of CADM1/TSLC1/IgSF4 expression in adult T-cell leukemia/lymphoma," *Leukemia*, 26, 2012, pp. 1238-1246.
Furuno et al., "The Spermatogenic Ig Superfamily/Synaptic Cell Adhesion Molecule Mast-Cell Adhesion Molecule Promotes Interaction with Nerves," *J. Immunol.*, 174, 2005, pp. 6934-6942.
Chilmi et al., "Development of anti-human CADM1 monoclonal antibodies as a potential therapy for adult T-cell leukemia/lymphoma," *International Journal Hematology*, 112, 2020, pp. 496-503.
International Search Report dated Jun. 28, 2022, issued in PCT/JP2022/019787, with English translation thereof.
International Preliminary Report on Patentability dated Nov. 14, 2023 and including Written Opinion dated Jun. 13, 2022, issued in PCT/JP2022/019787, with English translation thereof.
Office Action issued Nov. 26, 2024 in Japanese patent application No. 2023-521205, with English machine translation thereof.

*Primary Examiner* — Ruixiang Li
(74) *Attorney, Agent, or Firm* — Greenblum & Bernstein, P.L.C.

(57) ABSTRACT

It is an object of the present invention to provide an antibody that binds to CADM1 expressed on a cell, wherein the antibody alone is capable of inducing internalization of the antibody and the CADM1 into the cell. Specifically, the present invention relates to an antibody binding to CADM1 (Cell adhesion molecule 1), in which the antibody binds to CADM1 on the surface of a cell and induces internalization of the antibody and the CADM1 into the cell, or an antigen-binding fragment thereof. A representative example of the present antibody is an antibody having heavy chain CDR1 comprising the amino acid sequence as set forth in SEQ ID NO: 1, heavy chain CDR2 comprising the amino acid sequence as set forth in SEQ ID NO: 2, heavy chain CDR3 comprising the amino acid sequence as set forth in SEQ ID NO: 3, light chain CDR1 comprising the amino acid sequence as set forth in SEQ ID NO: 4, light chain CDR2 comprising the amino acid sequence as set forth in SEQ ID NO: 5, and light chain CDR3 comprising the amino acid sequence as set forth in SEQ ID NO: 6.

8 Claims, 12 Drawing Sheets

Specification includes a Sequence Listing.

[Figure 1a]
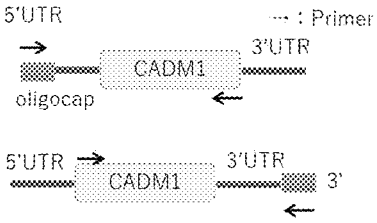
[Figure 1b]
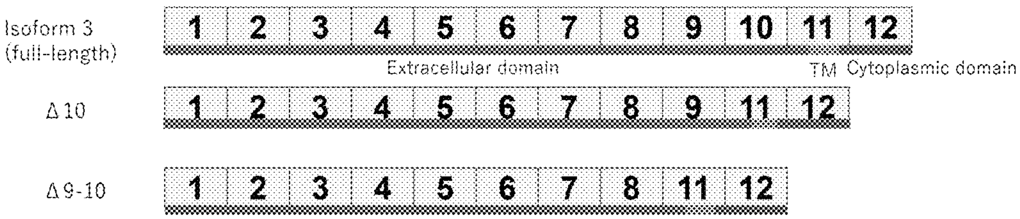
[Figure 2]
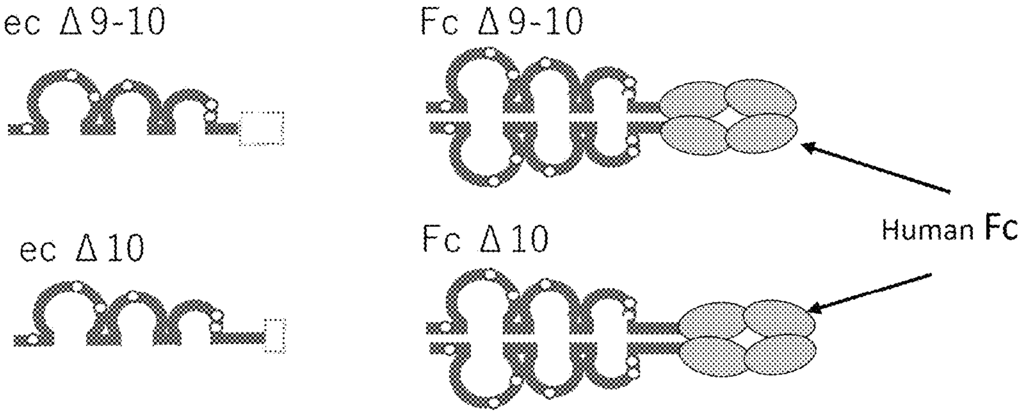

[Figure 3a]
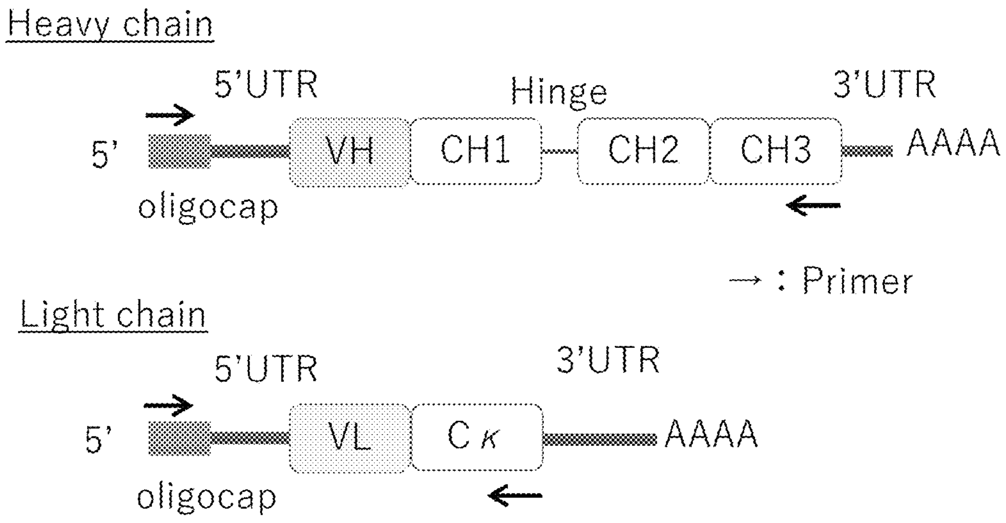
[Figure 3b]
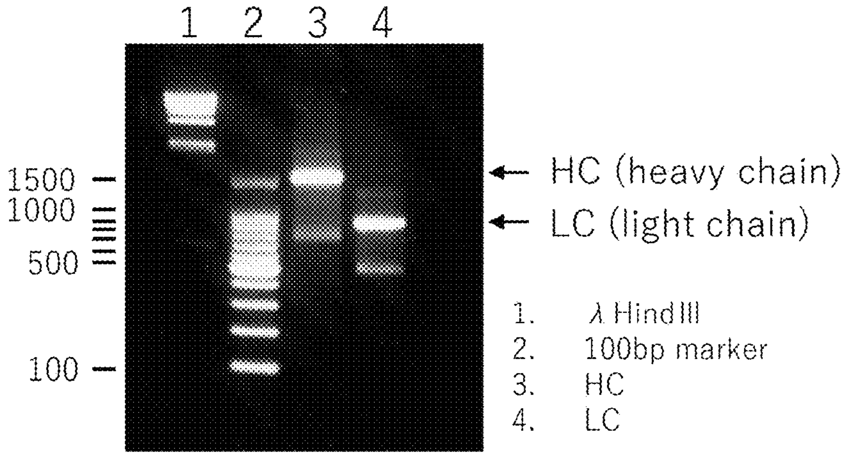

[Figure 4]
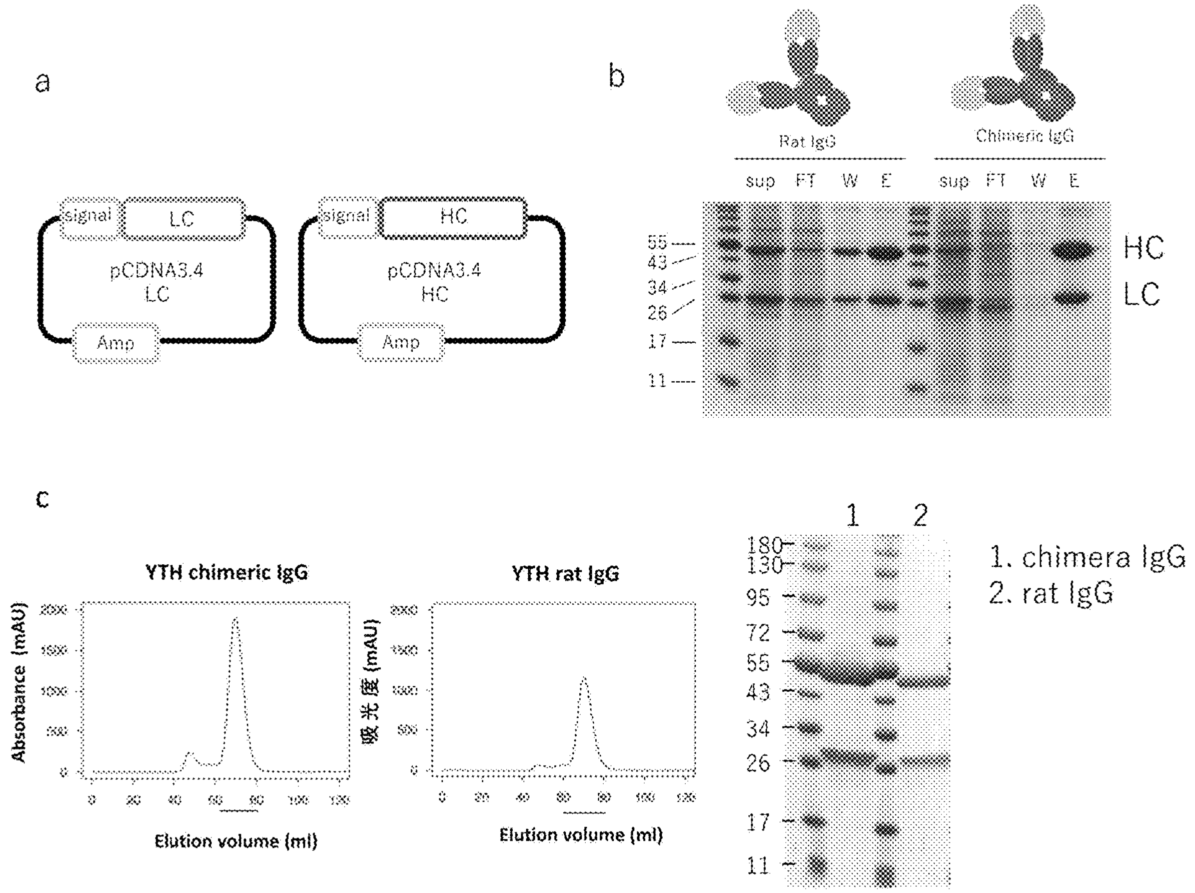

[Figure 5]
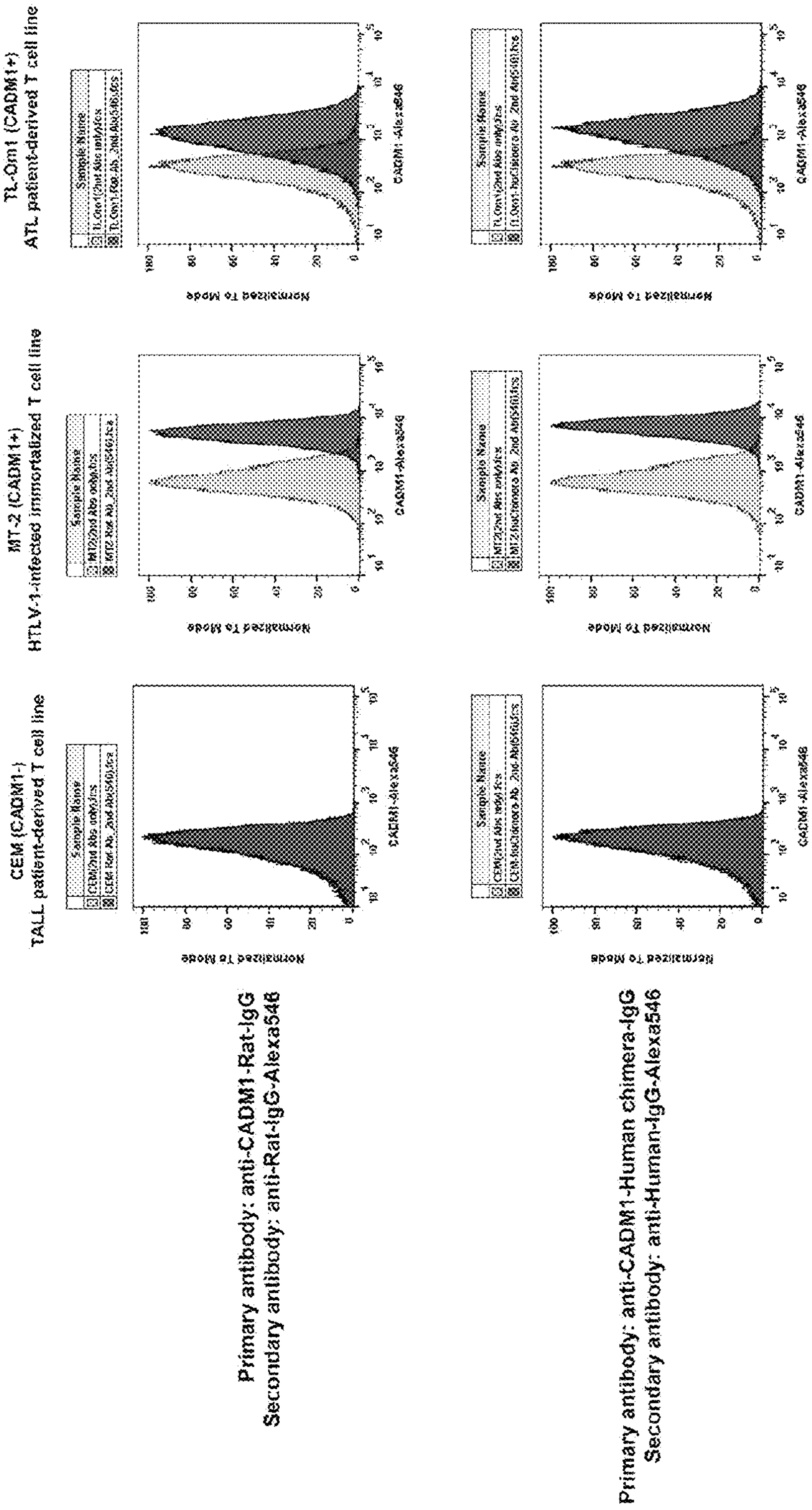

[Figure 6]
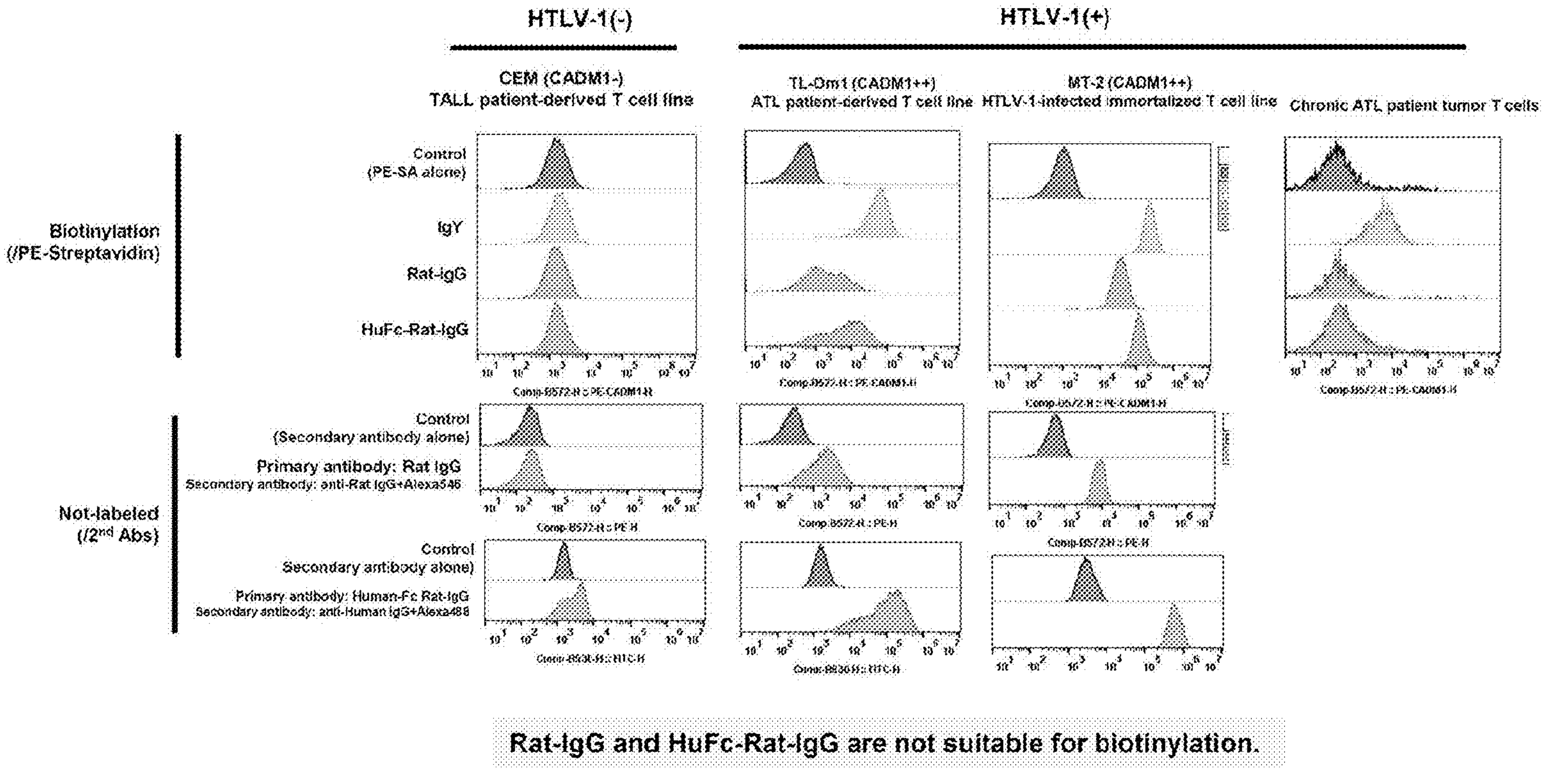

[Figure 7]
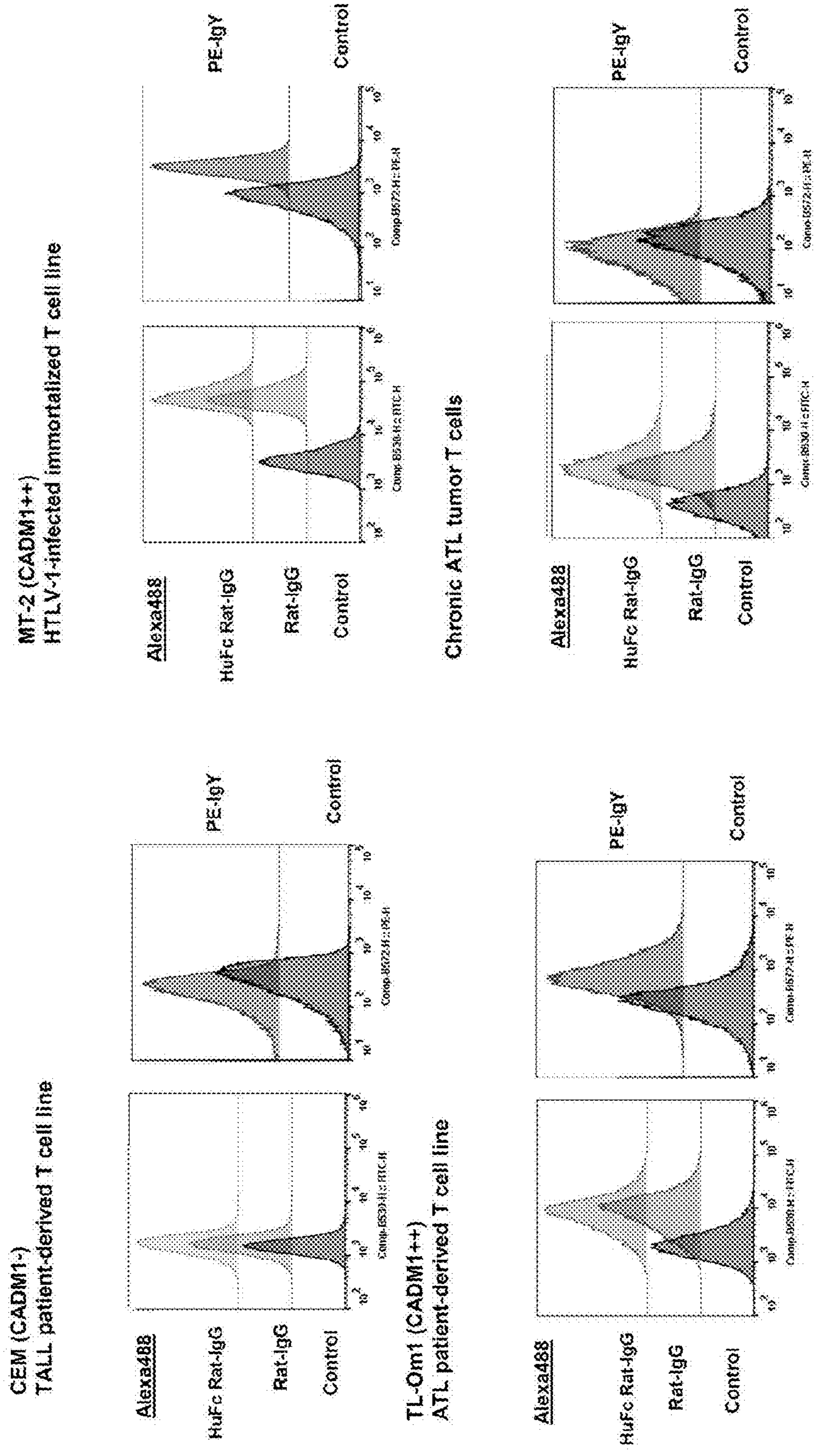

[Figure 8]
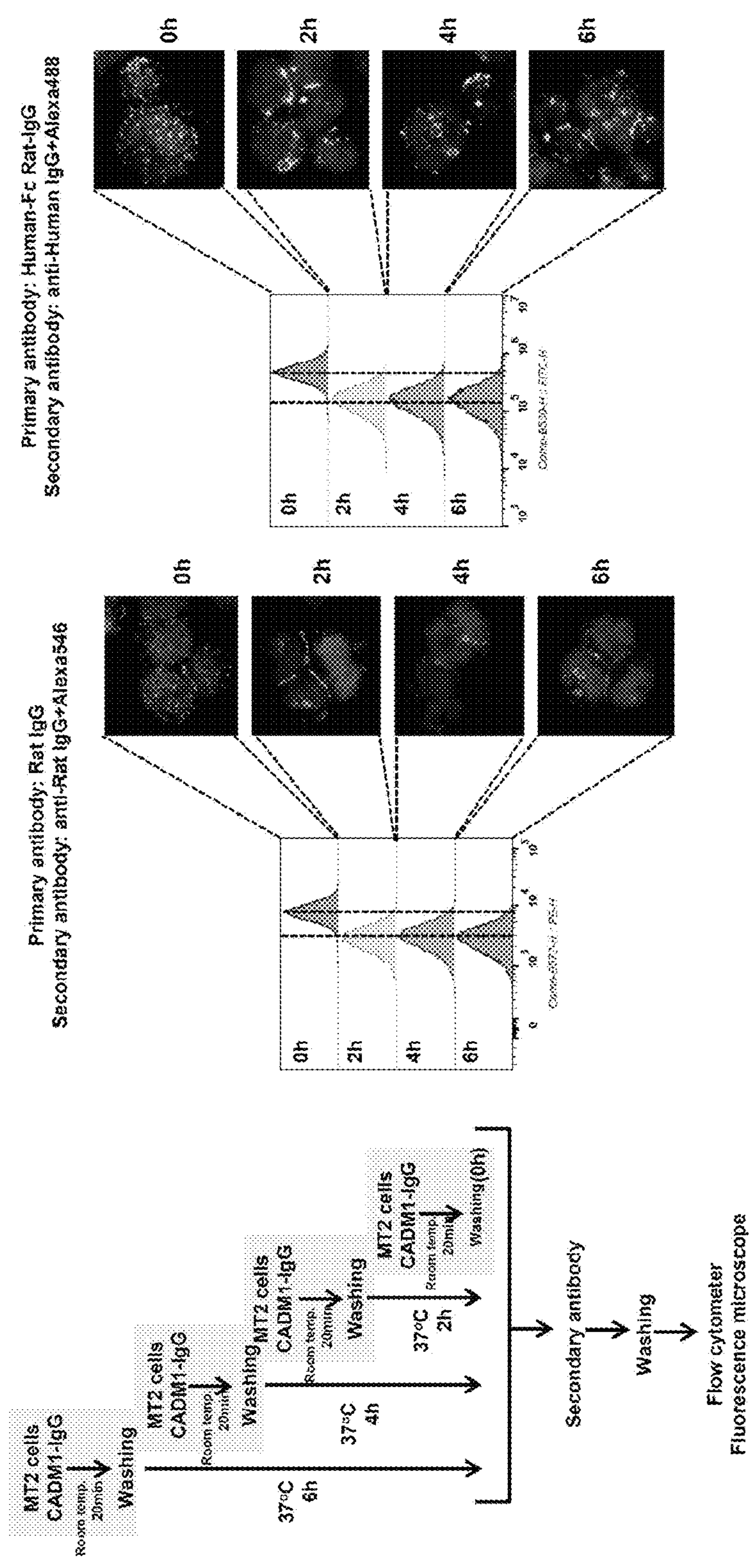

[Figure 9]
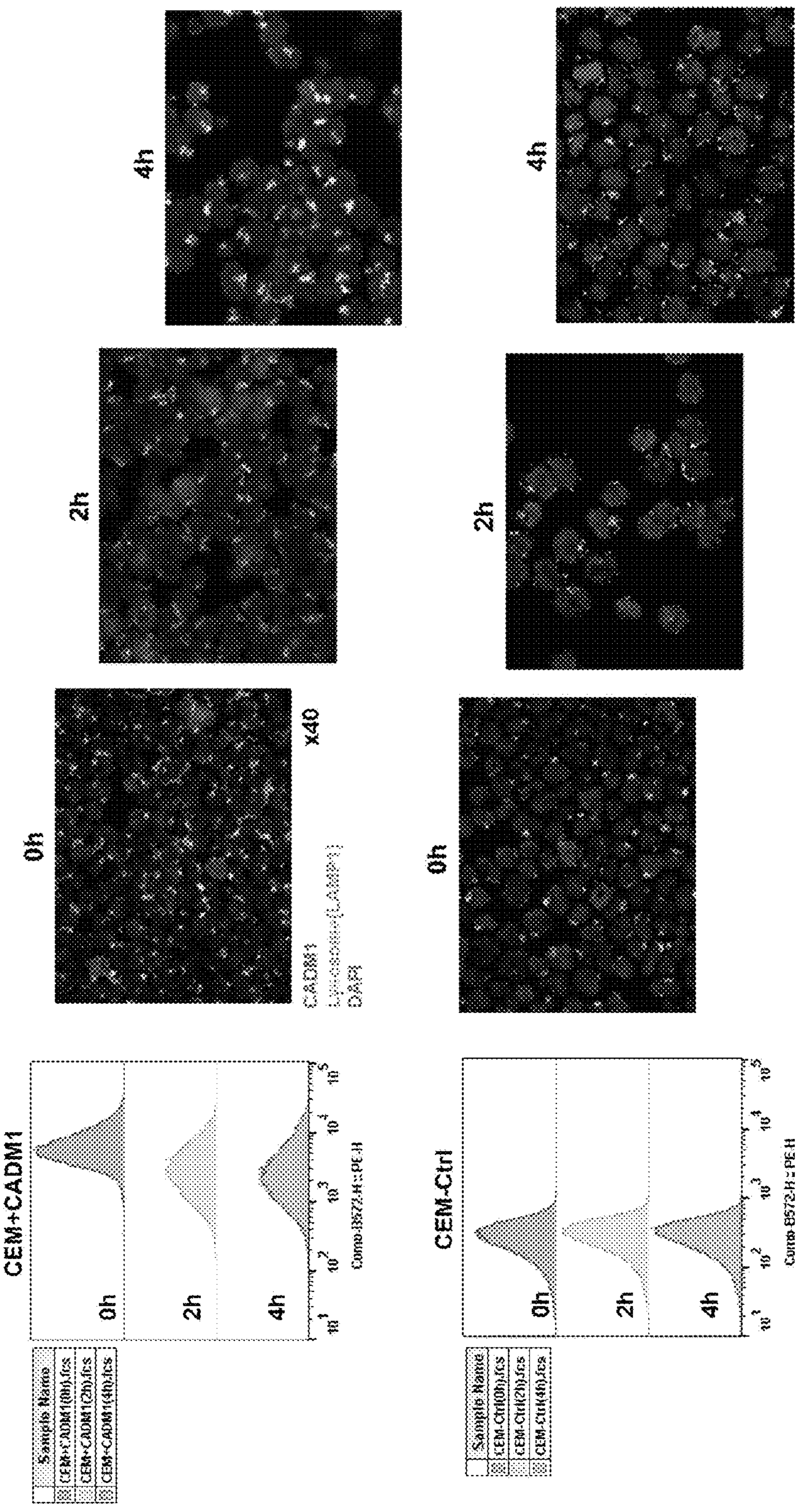

[Figure 10]
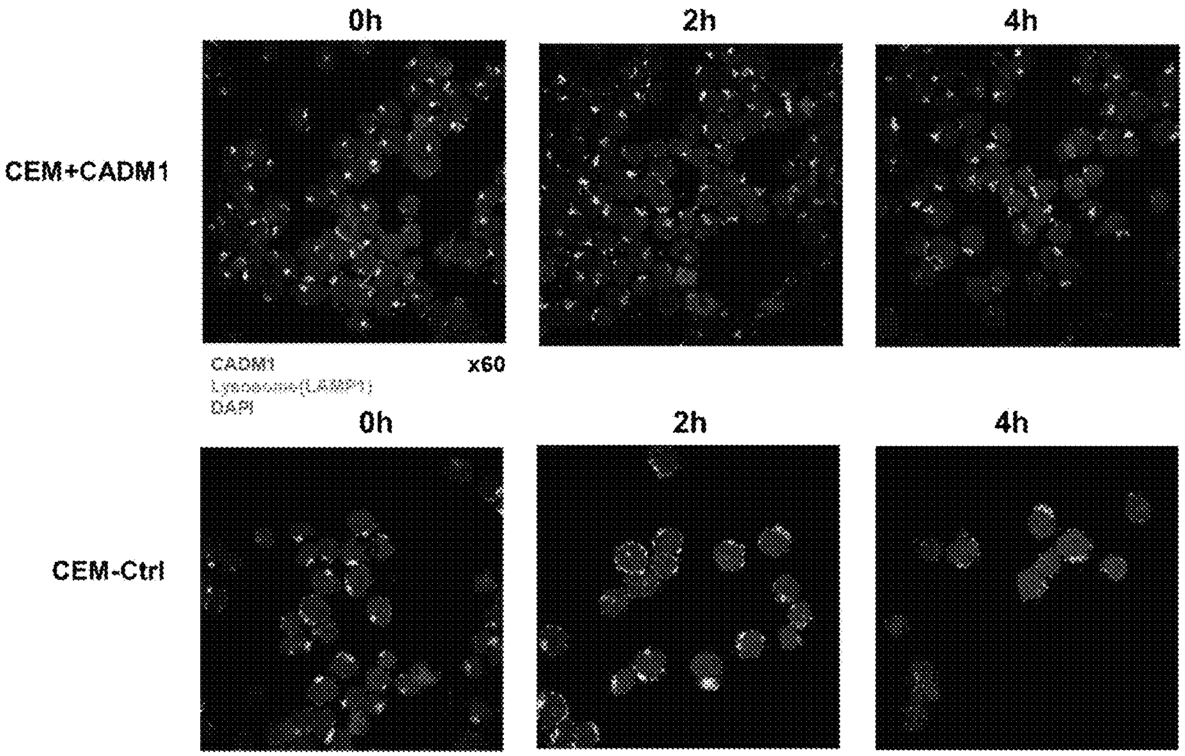

[Figure 11]
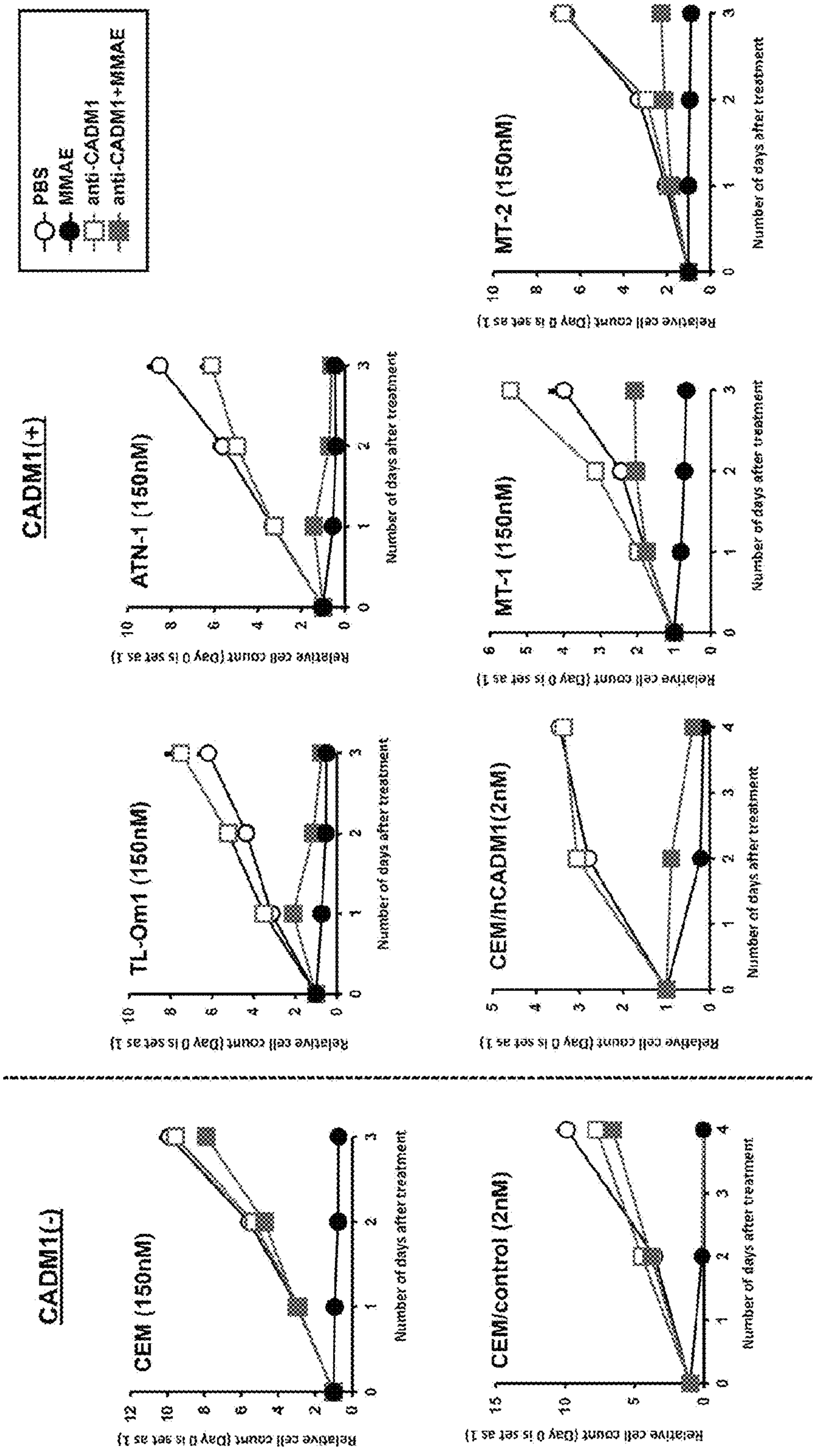

[Figure 12]
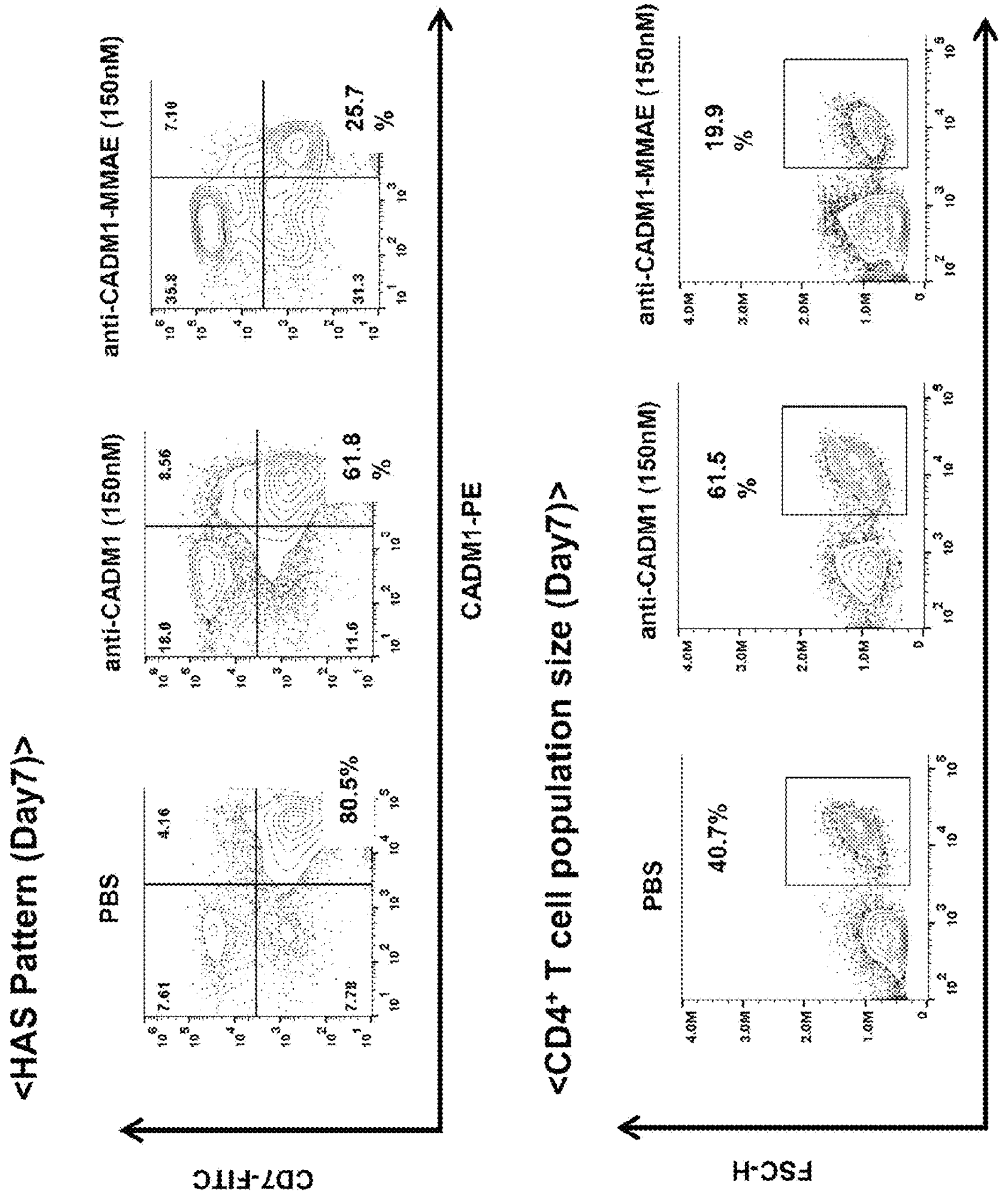

[Figure 13]
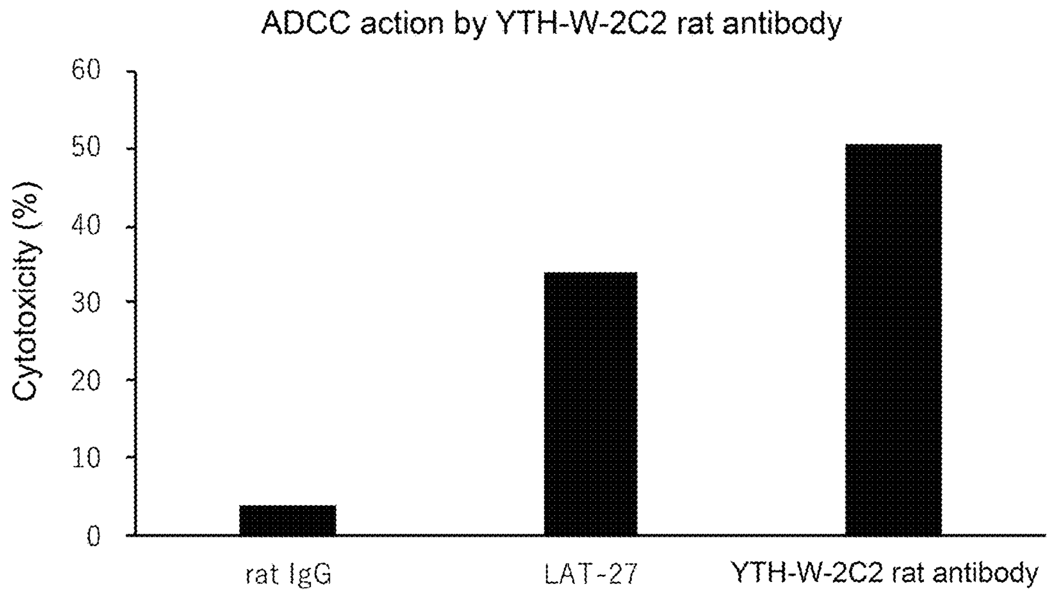
[Figure 14]
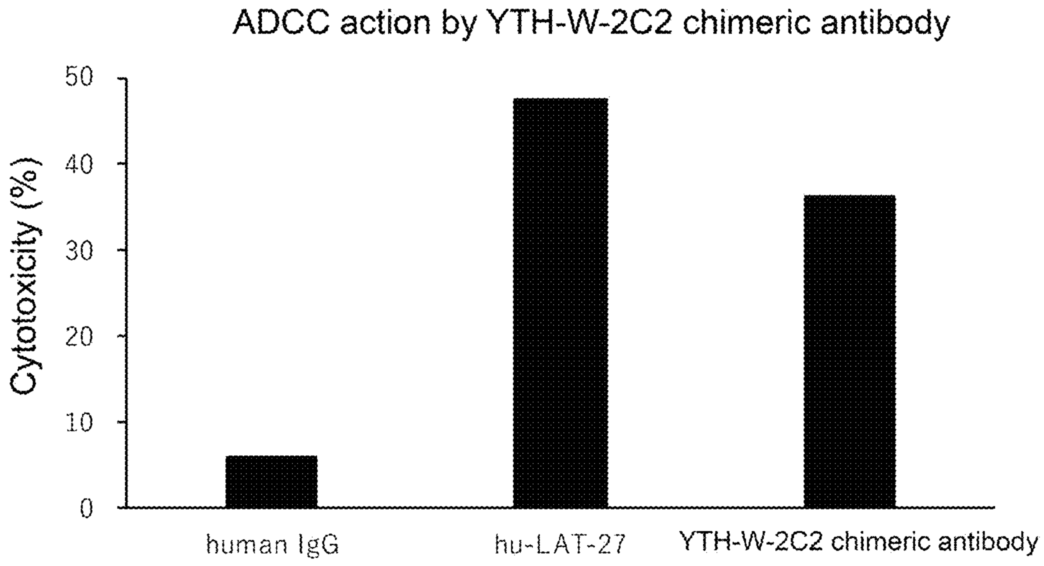

ANTI-CADM1 ANTIBODY

TECHNICAL FIELD

The present invention relates to an anti-CADM1 antibody. More specifically, the present invention relates to an antibody that binds to CADM1 on the surface of a cell and further internalizes the antibody itself and the CADM1 into the cell, and a fragment thereof, and the use thereof.

BACKGROUND ART

CADM1/TSLC1 (Cell adhesion molecule 1) is a molecule that has been identified as a tumor suppressor gene in lung cancer and belongs to the immunoglobulin superfamily cell adhesion molecules (Non Patent Literature 1). The expression of CADM1 is suppressed in epithelial cell-derived cancers such as lung non-small cell cancer, breast cancer, liver cancer, and pancreatic cancer.

On the other hand, it has been known that CADM1 is ectopically highly expressed in adult T-cell leukemia/lymphoma (ATLL) (Non Patent Literature 2 and Non Patent Literature 3). ATLL is a refractory peripheral T-cell tumor caused by infection with HTLV-1 (human T-cell leukemia virus type 1), but the details of the pathogenic mechanism thereof remain unknown, and the prognosis is extremely poor.

CADM1 that is highly expressed in ATLL is expected to be, not only for the rapid diagnosis of ATLL, but also as a target of treatments by DDS (Drug Delivery System), and thus, antibodies recognizing such CADM1 have been developed so far. For example, Furuno et al. have produced a chicken IgY antibody (9D2 clone) against SynCAM (synaptic cell adhesion molecule) (CADM1), and have reported that this antibody binds to CADM1 on the surface of a mast cell and inhibits the homophilic binding of the CADM1 (Non Patent Literature 4). Moreover, Patent Literature 1 discloses antibodies that specifically recognize IgSF4/TSLC1/CADM1 expressed on ATLL cells and are considered to be suitable for the diagnosis of ATLL. Although these antibodies can bind to CADM1 on the cells and thus, can be used for the diagnosis of ATLL, it is not unknown whether or not the antibodies can be used for treatments by DSS, for example, can be used as antibody-drug conjugates (ADCs). Antibodies suitable for use as ADCs must bind to antigens on the cell surface and then, must internalize the antibodies and the antigens into the cells.

Patent Literature 2 discloses an antibody (anti-CADM1 human IgG) that binds to CADM1 on a cancer cell and induces ADCC (antibody dependent cellular cytotoxicity). Patent Literature 2 discloses that cell death is induced when a saporin-conjugated anti-human IgG antibody (a conjugate of human IgG and saporin) is allowed to bind to the anti-CADM1 human IgG bound to the CADM1 on the cell. However, Patent Literature 2 does not disclose whether or not the anti-CADM1 human IgG alone can induce internalization of the anti-CADM1 human IgG and the CADM1.

As described above, among the previously reported anti-CADM1 antibodies, there are no antibodies that can induce internalization of the antibodies and the CADM1 into cells by themselves. Therefore, the development of antibodies that can be used for the treatment of diseases with ADCs still remains an issue to be achieved in the present field.

CITATION LIST

Patent Literature

Patent Literature 1: JP Patent Publication (Kokai) No. 2015-7030 A

Patent Literature 2: WO2010102175

Non Patent Literature

Non Patent Literature 1: Kuromachi et al., Nat Genet. 27: 427-430, 2001.

Non Patent Literature 2: Sasaki et al., Blood. 105: 1204-1213, 2005.

Non Patent Literature 3: Nakahata et al., Leukemia. 26: 1238-1246, 2012.

Non Patent Literature 4: Furuno et al., J. Immunol. 174: 6934-6942, 2005.

SUMMARY OF INVENTION

Technical Problem

Considering the aforementioned circumstances, it is an object of the present invention to develop an antibody that binds to CADM1 expressed on a cell and can induce internalization of the antibody and the CADM1 into the cell by the antibody itself.

Solution to Problem

The present inventors have attempted to prepare a monoclonal antibody by using 4 types of immunizing antigens, in which monomeric CADM1 and Fc-fused CADM1 capable of forming a dimer are mixed. As a result, the present inventors have succeeded in preparing an antibody exhibiting desired functions.

Specifically, the present invention includes the following (1) to (11).

(1) An antibody binding to CADM1 (Cell adhesion molecule 1), in which the antibody binds to CADM1 on the surface of a cell and induces internalization of the antibody and the CADM1 into the cell, or an antigen-binding fragment thereof.

(2) The antibody according to the above (1), characterized in that the amino acid sequences of CDRs (complementarity determining regions) 1-3 satisfy either the following (A) or (B), or an antigen-binding fragment thereof:

(A) the antibody has:

heavy chain CDR1 comprising the amino acid sequence as set forth in SEQ ID NO: 1, heavy chain CDR2 comprising the amino acid sequence as set forth in SEQ ID NO: 2, heavy chain CDR3 comprising the amino acid sequence as set forth in SEQ ID NO: 3, light chain CDR1 comprising the amino acid sequence as set forth in SEQ ID NO: 4, light chain CDR2 comprising the amino acid sequence as set forth in SEQ ID NO: 5, and light chain CDR3 comprising the amino acid sequence as set forth in SEQ ID NO: 6; or (B) the antibody has:

heavy chain CDR1 comprising the amino acid sequence as set forth in SEQ ID NO: 7, heavy chain CDR2 comprising the amino acid sequence as set forth in SEQ ID NO: 8, heavy chain CDR3 comprising the amino acid sequence as set forth in SEQ ID NO: 3, light chain CDR1 comprising the amino acid sequence as set forth in SEQ ID NO: 4, light chain CDR2 comprising the amino acid sequence as set forth in SEQ ID NO: 5, and light chain CDR3 comprising the amino acid sequence as set forth in SEQ ID NO: 6.

(3) The antibody according to the above (2), characterized in that the antibody satisfies either the following (a) or (b), or an antigen-binding fragment thereof:

(a) the antibody has a heavy chain variable region comprising the amino acid sequence as set forth in SEQ ID NO: 15, and a light chain variable region comprising the amino acid sequence as set forth in SEQ ID NO: 19; or (b) the antibody has a heavy chain variable region comprising an amino acid sequence having a sequence identity of 90% or more to the amino acid sequence as set forth in SEQ ID NO: 15, and a light chain variable region comprising an amino acid sequence having a sequence identity of 90% or more to the amino acid sequence as set forth in SEQ ID NO: 19.

(4) The antibody according to the above (2), characterized in that the CADM1 is dimerized on the cell surface, or an antigen-binding fragment thereof.

(5) An antibody binding to CADM1, which is characterized in that the antibody binds to CADM1 on the surface of a cell and induces internalization of the antibody and the CADM1 into the cell, and which competitively inhibits the binding between the antibody according to the above (2) and the CADM1, or an antigen-binding fragment thereof.

(6) The antibody according to the above (2), characterized in that the antibody is a humanized antibody or a chimeric antibody, or an antigen-binding fragment thereof.

(7) The antibody according to the above (2), characterized in that the antibody is a human antibody, or an antigen-binding fragment thereof.

(8) The antibody according to the above (2), characterized in that a substance having antitumor activity binds thereto, or an antigen-binding fragment thereof.

(9) The antigen-binding fragment according to the above (2), characterized in that the antigen-binding fragment is Fab, Fab', F $(ab')_2$, Fv, a single-chain antibody, scFv, scFv dimer, or dsFv.

(10) A pharmaceutical composition, comprising the antibody according to any one of the above (1) to (9) or an antigen-binding fragment thereof.

(11) The pharmaceutical composition according to the above (10), characterized in that the disease to be treated is adult T-cell leukemia/lymphoma.

It is to be noted that the preposition "to" sandwiched between numerical values is used in the present description to mean a numerical value range including the numerical values located left and right of the preposition.

Advantageous Effects of Invention

The antibody of the present invention has ADCC action. Furthermore, since the antibody of the present invention can bind to CADM1 on a cell and can induce internalization of the antibody and the CADM1 into the cell, the present antibody is expected to function as an antibody for ADC. In view of the above, the antibody of the present invention can exhibit effects as a therapeutic agent for ATLL and other diseases.

BRIEF DESCRIPTION OF DRAWINGS

FIG. 1 shows FIGS. 1*a* and 1*b* show the analysis of CADM1 variants. FIG. 1*a* shows the positions of primers set upon amplification of the CADM1 gene region by a 5' RACE method. FIG. 1*b* is a schematic view showing the gene structures of CADM1 isoform 3 (full length), exon 10-deficient variant (A10), and exon 9-10-deficient variant (49-10). TM: transmembrane domain.

FIG. 2 shows 4 types of immunizing antigens used to produce an anti-CADM1 antibody. FIG. 2 schematically shows the structures of the A10 variant (ecA10) and A9-10 variant (ecA9-10) of a CADM1 extracellular domain, a 410 variant dimerized via human Fc, and a 49-10 variant dimerized via human Fc.

FIG. 3 shows FIGS. 3*a* and 3*b* show the cloning of the variable regions of a rat anti-CADM1 antibody (YTH-W-2C2). FIG. 3*a* shows the positions of primers set upon amplification of the coding regions of the heavy and light chains of a YTH-W-2C2 antibody by a 5' RACE method. FIG. 3*b* shows the results of agarose gel electrophoresis performed on a PCR amplification product.

FIG. 4 shows FIGS. 4*a*, 4*b* and 4*c* show the expression and purification of recombinant antibodies. FIG. 4*a* schematically shows the structures of the expression constructs of an antibody light chain and an antibody heavy chain. FIG. 4*b* shows the SDS-PAGE profiles of a YTH-W-2C2 rat antibody and a YTH-W-2C2 chimeric antibody after affinity purification. FIG. 4*c* shows the absorbance (left) and SDS-PAGE (right) profiles of a YTH-W-2C2 rat antibody and a YTH-W-2C2 chimeric antibody purified by size exclusion chromatography.

FIG. 5 shows the results obtained by analyzing the binding ability of the antibody according to the embodiment of the present invention to a human T cell line, using a flow cytometer.

FIG. 6 shows the results obtained by labeling the antibody according to the embodiment of the present invention with a biotin, and then analyzing the binding ability of the antibody to the cells, using a flow cytometer.

FIG. 7 shows the results obtained by directly labeling the antibody according to the embodiment of the present invention with Alexa488, and then analyzing the binding ability of the antibody to the cells, using a flow cytometer.

FIG. 8 shows the results obtained by studying internalization of a conjugate of the antibody according to the embodiment of the present invention (Rat-IgG; YTH-W-2C2 rat antibody) and CADM1 into cells. FIG. 8 shows the analytical results obtained using a flow cytometer and the results obtained by the fluorescence microscopic observation of the cells.

FIG. 9 shows the results obtained by studying internalization of a conjugate of the antibody according to the embodiment of the present invention (Human-Fc-Rat-IgG; YTH-W-2C2 chimeric antibody) and CADM1 into cells. FIG. 9 shows the analytical results obtained using a flow cytometer and the results obtained by the fluorescence microscopic observation of the cells.

FIG. 10 shows the results obtained by observing the cells of FIG. 9 subjected to the fluorescence microscopic observation under a confocal laser microscope.

FIG. 11 shows the results obtained by studying production of ADC using the antibody according to the embodiment of the present invention (Human-Fc-Rat-IgG; YTH-W-2C2 chimeric antibody).

FIG. 12 shows the results obtained by analyzing the influence of ADC produced with the antibody according to the embodiment of the present invention (Human-Fc-Rat-IgG; YTH-W-2C2 chimeric antibody) on chronic ATL patient-derived ATL cells, using a flow cytometer.

FIG. 13 shows the results obtained by studying ADCC action using the antibody according to the embodiment of the present invention (YTH-W-2C2 rat antibody).

FIG. 14 shows the results obtained by studying ADCC action using the antibody according to the embodiment of the present invention (YTH-W-2C2 chimeric antibody).

DESCRIPTION OF EMBODIMENTS

A first embodiment of the present invention relates to an antibody binding to CADM1 (Cell adhesion molecule 1), in particular, to human CADM1, in which the antibody binds to CADM1 on the surface of a cell (in particular, CADM1 dimerized on the surface of a cell) and induces internalization of the antibody and the CADM1 into the cell (hereinafter also referred to as "the anti-CADM1 antibody according to the present embodiment"), or an antigen-binding fragment thereof.

The anti-CADM1 antibody according to the present embodiment can be prepared, for example, as follows, although the preparation method is not particularly limited thereto. There can be used 4 types of immunizing antigens, in which monomeric CADM1 and Fc-fused CADM1 capable of forming a dimer are mixed. Specifically, a mixture consisting of 4 types of proteins, namely, a Δ9-10 variant of a CADM1 extracellular domain, a Δ10 variant of a CADM1 extracellular domain, a Δ9-10 Fc variant formed by fusing a CADM1 extracellular domain with human Fc, and a Δ10 Fc variant formed by fusing a CADM1 extracellular domain with human Fc, can be used as an immunizing antigen. For details, please refer to Examples described later.

The "antibody" mentioned in the present description is not particularly limited in terms of the preparation method thereof and the structure thereof, and includes all "antibodies" that bind to desired antigens by desired properties, such as, for example, monoclonal antibodies, polyclonal antibodies, or nanoantibodies.

When the anti-CADM1 antibody according to the present embodiment is a polyclonal antibody, it can be prepared, for example, by injecting a mixture of an antigen and an adjuvant into an animal to be immunized (although it is not limited, but it is, for example, a rabbit, a goat, sheep, a chicken, a guinea pig, a mouse, a rat or a pig, etc.). Usually, an antigen and/or an adjuvant are injected into the subcutis or abdominal cavity of an animal to be immunized multiple times. Examples of the adjuvant may include, but are not limited to, a complete Freund's adjuvant and monophosphoryl lipid A synthetic-trehalose dicolinomicolate (MPL-TMD). After immunization with the antigen, an anti-CADM1 antibody can be purified from the serum derived from the immunized animal according to a usual method (for example, a method using Protein A-retaining Sepharose, etc.), or other methods.

On the other hand, when the anti-CADM1 antibody according to the present embodiment is a monoclonal antibody, it can be prepared, for example, as follows. Besides, the term "monoclonal" is used in the present description to suggest the properties of an antibody obtained from a substantially homogeneous population of antibodies (a population of antibodies, in which the amino acid sequences of the heavy and light chains constituting the antibodies are identical to one another), and thus, the term "monoclonal" should not be interpreted limitedly, such that the antibody is produced by a specific method (e.g., a hybridoma method, etc.).

Examples of the method for producing a monoclonal antibody may include a hybridoma method (Kohler and Milstein, Nature 256, 495-497, 1975) and a recombination method (U.S. Pat. No. 4,816,567). Otherwise, the anti-CADM1 antibody according to the present embodiment may be isolated from a phage antibody library (e.g. Clackson et al., Nature, 352 624-628, 1991; Marks et al., J. Mol. Biol. 222, 581-597, 1991; etc.) or the like. More specifically, when a monoclonal antibody is prepared using a hybridoma method, the preparation method comprises, for example, the following 4 steps: (i) immunizing an animal to be immunized with an antigen; (ii) recovering monoclonal antibody-secreting (or potentially secreting) lymphocytes; (iii) fusing the lymphocytes with immortalized cells; and (iv) selecting cells that secrete a desired monoclonal antibody. As such an animal to be immunized, for example, a mouse, a rat, a guinea pig, a hamster, a rabbit or the like can be selected. After completion of the immunization, in order to establish hybridoma cells, lymphocytes obtained from the host animal are fused with an immortalized cell line, by using a fusion agent such as polyethylene glycol or an electrical fusion method. As fusion cells, a rat or mouse myeloma cell line is used, for example. After completion of the cell fusion, the cells are allowed to grow in a suitable medium that contains a substrate that inhibits the growth or survival of unfused lymphocytes and immortalized cell line. According to an ordinary technique, parent cells that lack the enzyme, hypoxanthine-guanine phosphoribosyl transferase (HGPRT or HPRT), are used. In this case, aminopterin is added to a medium that inhibits the growth of the HGPRT-deficient cells and allows the growth of hybridomas (HAT medium). From the thus obtained hybridomas, those producing desired antibodies can be selected, and then, a monoclonal antibody of interest can be obtained from a medium, in which the selected hybridomas grow, according to an ordinary method.

The thus prepared hybridomas are cultured in vitro, or are cultured in vivo in the ascites of a mouse, a rat, a guinea pig, a hamster, etc., so that an antibody of interest can be prepared from a culture supernatant or ascites.

The nanoantibody is a polypeptide consisting of the variable region of an antibody heavy chain (i.e. the variable domain of the heavy chain of a heavy chain antibody; VHH). In general, an antibody of a human or the like is composed of a heavy chain and a light chain. However, camelids such as llamas, alpacas and camels produce a single-chain antibody only consisting of a heavy chain (i.e., a heavy-chain antibody). Such a heavy-chain antibody can recognize a target antigen and can bind to the antigen, as in the case of an ordinary antibody consisting of a heavy chain and a light chain. The variable region of the heavy chain is a minimum unit having binding affinity for an antigen, and this variable domain fragment is referred to as a "nanoantibody." The nanoantibody has high heat resistance, digestion resistance and normal temperature resistance, and thus, it is possible to more easily prepare a large amount of the nanoantibody according to a genetic engineering method.

The nanoantibody can be produced, for example, as follows. A camelid is immunized with an antigen, and then, the presence or absence of an antibody of interest is detected in the collected serum. Thereafter, cDNA is produced from RNA derived from the peripheral blood lymphocytes of the immunized animal, in which a desired antibody titer is detected. A DNA fragment encoding VHH is amplified from the obtained cDNA, and is then inserted into a phagemid to prepare a VHH phagemid library. A desired nanoantibody can be produced from the prepared VHH phagemid library through several times of screening.

The anti-CADM1 antibody according to the present embodiment may be a genetically recombinant antibody. An example of such a genetically recombinant antibody may be, but is not limited to, a chimeric antibody consisting of a humanized antibody and a human antibody. The chimeric antibody means an antibody in which a variable region derived from an animal is ligated to a constant region derived from a different animal (for example, an antibody, in which a rat-derived antibody variable region is ligated to a human-derived antibody constant region) and the like (e.g. Morrison et al., Proc. Natl. Acad. Sci. U.S.A. 81, 6851-6855 1984., etc.), and such a chimeric antibody can be easily constructed by a genetic recombination technique.

The humanized antibody is an antibody having a human-derived sequence in the framework region (FR) thereof and having a complementarity determining region (CDR) derived from another animal species (e.g., a mouse). Using herein a mouse as an example of another animal species, the humanized antibody can be produced by first transplanting the CDRs of the variable region of an antibody derived from a mouse into a human antibody variable region, then reconstituting the heavy chain and light chain variable regions, and then linking these humanized reconstituted human antibody variable regions to human antibody constant regions. The methods for producing such a humanized antibody is well known in the present technical field (e.g. Queen et al., Proc. Natl. Acad. Sci. USA, 86, 10029-10033, 1989., etc.).

The antigen-binding fragment of the antibody of the present invention means a partial region of the antibody of the present invention, which is an antibody fragment binding to human CADM1. Examples of such an antigen-binding fragment may include Fab, Fab', $F(ab')_2$, Fv (a variable fragment of an antibody), a single-chain antibody (a heavy chain, a light chain, a heavy chain variable region, a light chain variable region, a nanoantibody, etc.), scFv (single chain Fv), a diabody (an scFv dimer), dsFv (disulfide-stabilized Fv), and a peptide comprising the CDR of the antibody of the present invention in at least a portion thereof.

Fab is an antibody fragment having antigen-binding activity obtained by digesting an antibody molecule with the protease papain, wherein about an N-terminal half of the heavy chain binds to the light chain as a whole via a disulfide bond. Fab can be produced by digesting an antibody molecule with papain to obtain a fragment thereof. Fab can also be produced by, for example, constituting a suitable expression vector into which DNA encoding the Fab has been inserted, then introducing the vector into suitable host cells (e.g. mammalian cells such as CHO cells, yeast cells, insect cells, etc.), and then allowing it to express in the cells.

$F(ab')_2$ is an antibody fragment having antigen-binding activity obtained by digesting an antibody molecule with the protease pepsin, which is slightly greater than Fab that binds to another Fab via a disulfide bond at hinge region. $F(ab')_2$ can be obtained by digesting an antibody molecule with the pepsin, or it can also be produced by binding Fab to another Fab via a thioether bond or a disulfide bond. Alternatively, F(ab')2 can also be produced according to a genetic engineering method, as with Fab.

Fab' is an antibody fragment having antigen-binding activity obtained by cleaving the disulfide bond at hinge region of the above-described F(ab')2. Fab' can also be produced according to a genetic engineering method, as in the case of Fab and the like.

scFv is an antibody fragment having antigen-binding activity that is a VH-linker-VL or VL-linker-VH polypeptide, wherein a single heavy chain variable region (VH) is ligated to a single light chain variable region (VL) using a suitable peptide linker. Such scFv can be produced by obtaining cDNAs encoding the heavy chain variable region and light chain variable region of an antibody and then treating them according to a genetic engineering method.

Diabody is an antibody fragment having divalent antigen-binding activity, in which scFv is dimerized. Regarding the divalent antigen-binding activity, this activity may be an activity of binding to either two identical antigens, or two different antigens. The diabody can be produced by obtaining cDNAs encoding the heavy chain variable region and light chain variable region of an antibody, then constructing cDNA encoding scFV, in which the heavy chain variable region is ligated to the light chain variable region using a peptide linker, and then treating the cDNA according to a genetic engineering method.

dsFv is a polypeptide which comprises a heavy chain variable region and a light chain variable region each including a substitution of one amino acid residue with a cysteine residue, in which VH binds to VL via a disulfide bond between the cysteine residues. The amino acid residue to be substituted with the cysteine residue can be selected based on prediction of the three-dimensional structure of antibodies. Such dsFv can be produced by obtaining cDNAs encoding the heavy chain variable region and light chain variable region of the antibody and then constructing DNA encoding the dsFv according to a genetic engineering method.

A peptide comprising CDR is constituted such that it comprises at least one region of CDR (CDR1-3) of the heavy chain or light chain. A peptide, which comprises multiple CDR regions, is able to bind to another peptide directly or via a suitable peptide linker. In the case of a peptide comprising CDR, DNA encoding the CDR of the heavy chain or light chain of the antibody is constructed, and it is then inserted into an expression vector. The type of the vector is not particularly limited, and it may be selected, as appropriate, depending on the type of a host cells into which the vector is to be introduced, and the like. The vector is introduced into host cells suitable for the expression of an antibody (e.g. mammalian cells such as CHO cells, yeast cells, insect cells, etc.), so that the peptide can be produced. Alternatively, such a peptide comprising CDR can also be produced by chemical synthesis methods such as an Fmoc method (fluorenylmethyloxycarbonyl method) and a tBoc method (t-butyloxycarbonyl method).

A human antibody (complete human antibody) generally has the same structure as the antibody of a human, in terms of the structures of a hypervariable region as an antigen-binding site in the V region), other parts in the V region, and a constant region. The human antibody can be easily produced by those skilled in the art using known techniques. The human antibody can be obtained, for example, by a method using a human antibody-producing mouse having a human chromosome fragment containing the H- and L-chain genes of a human antibody (e.g., Tomizuka et al., Proc. Natl. Acad. Sci. USA, 97, 722-727, 2000, etc.) or a method of obtaining a human antibody derived from a phage display selected from a human antibody library (see, for example, Siriwardena et al., Opthalmology, 109, 427-431, 2002, etc.).

The antigen-binding fragment of the antibody of the present invention can be used to construct a multispecific antibody. Multispecificity means that an antibody has binding specificity to two or more antigens, and such multispecificity may be, for example, the form of a protein comprising a monoclonal antibody or an antigen-binding fragment, having binding specificity to two or more antigen. This multispecific antibody can be obtained by those skilled in the art using known techniques. Several methods have been developed as methods for constituting multispecificity, and such methods can be classified into: techniques of constructing asymmetric IgG, in which protein engineering operations are performed on two different types of antibody heavy chain molecules to allow the molecules to form a heterodimer; techniques of linking low-molecular-weight antigen-binding fragments obtained from an antibody to each other or linking the low-molecular-weight antigen-binding fragment to another antibody molecule; and other techniques. As an example of a specific construction method, for example, the following publication can be referred to: Kontermann et al., Drug Discovery Today, 20, 838-847, 2015.

Examples of the anti-CADM1 antibody according to the present embodiment and an antigen-binding fragment thereof may include an anti-CADM1 antibody characterized in that the amino acid sequences of CDRs (complementarity determining regions) 1-3 satisfy either the following (A) or (B), and an antigen-binding fragment thereof:

(A) the antibody has:

the amino acid sequence of heavy chain CDR1 being NYDIS (SEQ ID NO: 1), the amino acid sequence of heavy chain CDR2 being YIHTGSGGTYYNEKFKG (SEQ ID NO: 2), the amino acid sequence of heavy chain CDR3 being TPYVYYGSGYFDF (SEQ ID NO: 3), the amino acid sequence of light chain CDR1 being KSSQSLLYSGNQKNYLA (SEQ ID NO: 4), the amino acid sequence of light chain CDR2 being WASTRQS (SEQ ID NO: 5), and the amino acid sequence of light chain CDR3 being QQYYDTPDT (SEQ ID NO: 6); or (B) the antibody has:

the amino acid sequence of heavy chain CDR1 being GYTFSNY (SEQ ID NO: 7), the amino acid sequence of heavy chain CDR2 being HTGSGG (SEQ ID NO: 8), the amino acid sequence of heavy chain CDR3 being TPYVYYGSGYFDF (SEQ ID NO: 3), the amino acid sequence of light chain CDR1 being KSSQSLLYSGNQKNYLA (SEQ ID NO: 4), the amino acid sequence of light chain CDR2 being WASTRQS (SEQ ID NO: 5), and the amino acid sequence of light chain CDR3 being QQYYDTPDT (SEQ ID NO: 6).

Furthermore, other examples of the anti-CADM1 antibody according to the present embodiment and an antigen-binding fragment thereof may include: an antibody having any of a heavy chain variable region comprising the amino acid sequence as set forth in SEQ ID NO: 15 and a light chain variable region comprising the amino acid sequence as set forth in SEQ ID NO: 19; and an antibody consisting of an amino acid sequence having an amino acid sequence identity of about 70% or more, preferably about 80% or more, about 81% or more, about 82% or more, about 83% or more, about 84% or more, about 85% or more, about 86% or more, about 87% or more, about 88% or more, about 89% or more, more preferably about 90% or more, about 91% or more, about 92% or more, about 93% or more, about 94% or more, about 95% or more, about 96% or more, about 97% or more, about 98% or more, and most preferably about 99% or more, to the amino acid sequence of each of the heavy chain variable region and/or the light chain variable region that constitute the aforementioned antibody, wherein the antibody binds to CADM1 on the surface of a cell and induces internalization of the antibody and the CADM1 into the cell, or an antigen-binding fragment thereof.

A second embodiment of the present invention relates to an antibody binding to CADM1, which is characterized in that the antibody binds to CADM1 on the surface of a cell and induces internalization of the antibody and the CADM1 into the cell, and which competitively inhibits the binding between the antibody according to the first embodiment (i.e. the anti-CADM1 antibody according to the present embodiment) and the CADM1 (hereinafter also referred to as "the competitive antibody according to the present embodiment"), or an antigen-binding fragment thereof. The competitive antibody according to the present embodiment can be prepared and obtained by performing competitive experiments etc. that are well known to those skilled in the art. Specifically, when the binding between a first anti-CADM1 antibody (the antibody according to the first embodiment) and CADM1 is competitively inhibited by a second anti-CADM1 antibody, it is determined that the first anti-CADM1 antibody and the second anti-CADM1 antibody bind to antigen sites that are substantially identical to each other, or are extremely close to each other. Also, when the second anti-CADM1 antibody has the function to bind to CADM1 on the surface of a cell and to induce internalization of the second anti-CADM1 antibody and the CADM1 into the cell, the second anti-CADM1 antibody is the competitive antibody according to the present embodiment. As a method of such a competitive experiment, for example, a method using a Fab fragment, etc. is generally applied in the present technical field. Please refer to, for example, WO95/11317, WO94/07922, WO2003/064473, WO2008/118356 and WO2004/046733, etc.

A third embodiment of the present invention relates to the antibody according to the first embodiment or the antibody according to the second embodiment, to which a substance having antitumor activity, particularly preferably, a substance having antitumor activity against adult T-cell leukemia/lymphoma binds, or an antigen-binding fragment thereof.

A substance having antitumor activity, such as a drug, is allowed to bind to an antibody, and targeted therapy for cancer can be carried out (hereinafter, such a conjugate is also referred to as a "conjugate of an antibody and a drug, etc."). In this case, the substances having antitumor activity include cytotoxic drugs such as anticancer agents, radioisotopes, and substances that indirectly induce antitumor activity by manipulating the immune system, but are not limited thereto.

In the third embodiment, a drug exhibiting antitumor activity can be used, and such a conjugate is called an antibody-drug conjugate. Examples of the known drug exhibiting antitumor activity as used herein may include tubulin inhibitors and microtubule polymerization inhibitors, such as Auristatins (MMAE, MMAF, etc.), Maytansines (DM1, DM4, etc.), Tubulysins, cryptophycins and rhizoxin, antibiotics such as Calicheamicins, Doxorubicin and anthracyclines, DNA synthesis inhibitors such as Duocarmycins, PBDs (Benzodiazepines) and IGNs (indolinobenzodiazepines), topoisomerase I inhibitors such as Canptothecin analogs (SN-38, DXd, etc.), RNA polymerase II inhibitors such as Amanitins, RNA spliceosome inhibitors such as spliceostatins and thailanstatins, and apoptosis-related protein inhibitors, but the examples of the drug exhibiting antitumor activity are not limited thereto (for details, see, for example, Yaghoubi et al., J Cell Physiol. 235: 31-64, 2020. doi:10.1002/jcp.28967, etc.).

Moreover, as such a drug exhibiting antitumor activity, a compound that is excited by light energy and expresses toxicity can also be used. Such an antibody-drug conjugate can be used in a therapy called photoimmunotherapy (PIT) (Kobayashi et al., Int Immunol. 33: 7-15, 2021), in which the conjugate is administered into a body and is allowed to bind to tumor cells, and the conjugate then kills the tumor cells by applying light energy such as near-infrared rays from outside the body. The anti-CADM1 antibody according to the present embodiment may also be used as an antibody for the photoimmunotherapy. As a compound used, IRDye 700DX, etc. has been known, but the compound is not limited thereto.

A large number of chemical modification methods of binding an antitumor substance to an antibody have been known, and for example, the following methods have been known. That is, examples of the chemical modification methods may include: chemical modification methods such as covalent bonding to lysine residue side chains and covalent bonding to cysteine residue side chains; a method of introducing non-natural amino acids into the peptide chain of an antibody, and performing a site-specific chemical modification on the side chains; a method of modifying a specific amino acid sequence in an antibody or a modified sugar chain by using an enzyme reaction specific to the amino acid sequence or the sugar chain; and a modification method using an enzyme for peptide linkage. Moreover, in order to allow a drug or the like to bind to a protein, it is general to perform a chemical modification on a drug or the like and to use the drug as a linker for protein binding. Many types of such chemical linkers have been known, and depending on their properties, the pharmacological action of the conjugate of an antibody and a drug, etc. in a body is greatly changed. For example, a hydrazone linker, a valine-citrulline linker, an SS bond linker, a pyrophosphoric acid linker, etc. are cleaved by enzymes in a body, and the drug is separated from the antibody, so that an antibody-drug conjugate exhibiting high antitumor effects can be prepared. On the other hand, a chemical structure that cannot be cleaved in a body is also generally used as such a chemical linker. An overview of the above-mentioned methods is described, for example, in the following publication: Tsuchikama and An, Protein and Cell, 9, 33-46, 2018.

A fourth embodiment of the present invention relates to a pharmaceutical composition comprising the conjugate of an antibody and a drug, etc. or an antigen-binding fragment thereof according to the third embodiment, wherein the pharmaceutical composition is for use in the prevention or treatment of cancer, particularly preferably, adult T-cell leukemia/lymphoma (hereinafter also referred to as "the pharmaceutical composition according to the present embodiment").

The pharmaceutical composition according to the present embodiment may be administered in the form of a pharmaceutical composition comprising 1 or 2 or more pharmaceutical additives, as well as the conjugate of an antibody and a drug, etc. or an antigen-binding fragment thereof that serves as an active ingredient. Also, other known drugs may be mixed into the pharmaceutical composition according to the present embodiment.

The pharmaceutical composition according to the present embodiment may have either an oral or parenteral dosage form, and the dosage form of the present pharmaceutical composition is not particularly limited. Examples of the dosage form thereof may include a tablet, a capsule, a granule, a powder agent, a syrup agent, a suspending agent, a suppository, an ointment, a cream agent, a gelling agent, a patch, an inhalant, and an injection. These formulations are prepared according to ordinary methods. In the case of a liquid formulation, it may be dissolved or suspended in water or other suitable solvents upon use. In addition, a tablet or a granule may be coated according to publicly known methods. In the case of an injection, it is prepared by dissolving the antibody according to the present embodiment or a functional fragment thereof in water. Such an injection may also be prepared by dissolving the antibody according to the present embodiment or a functional fragment thereof in a normal saline or a glucose solution, as necessary. Otherwise, a buffer or a preservative may also be added to the injection.

The types of the pharmaceutical additives used in production of the pharmaceutical composition according to the present embodiment, the ratio of the pharmaceutical additives to the active ingredient, or the method for producing the pharmaceutical composition can be selected, as appropriate, by those skilled in the art, depending on the form of the present pharmaceutical composition. As pharmaceutical additives, inorganic or organic substances, or solid or liquid substances can be used. In general, such pharmaceutical additives can be mixed into the present pharmaceutical composition, in an amount of, for example, 0.1% by weight to 99.9% by weight, 1% by weight to 95.0% by weight, or 1% by weight to 90.0% by weight, based on the weight of the active ingredient. Specific examples of the pharmaceutical additives may include lactose, glucose, mannitol, dextrin, cyclodextrin, starch, sucrose, magnesium aluminometasilicate, synthetic aluminum silicate, carboxymethyl cellulose sodium, hydroxypropyl starch, carboxymethyl cellulose calcium, ion exchange resin, methyl cellulose, gelatin, gum Arabic, hydroxypropyl cellulose, hydroxypropylmethyl cellulose, polyvinyl pyrrolidone, polyvinyl alcohol, light anhydrous silicic acid, magnesium stearate, talc, tragacanth, bentonite, beegum, titanium oxide, sorbitan fatty acid ester, sodium lauryl sulfate, glycerin, fatty acid glycerin ester, purified lanolin, glycerogelatin, polysorbate, macrogol, vegetable oil, wax, liquid paraffin, white petrolatum, fluorocarbon, nonionic surfactant, propylene glycol, and water.

In order to produce a solid formulation for oral administration, the active ingredient is mixed with excipient components such as, for example, lactose, starch, crystalline cellulose, calcium lactate, or anhydrous silicic acid to prepare a powder agent. Otherwise, as necessary, binders such as white sugar, hydroxypropyl cellulose or polyvinyl pyrrolidone, disintegrators such as carboxymethyl cellulose or carboxymethyl cellulose calcium, and the like are further added to the aforementioned mixture, and the thus obtained mixture is then subjected to wet or dry granulation, so as to prepare a granule. In order to produce a tablet, these powder agents and granules may be directly subjected to tablet making, or these powder agents and granules, together with a lubricant such as magnesium stearate or talc, may be subjected to tablet making. These granules or tablets can be processed into enteric-coated formulations by being coated with enteric-coating base agents such as hydroxypropylmethyl cellulose phthalate or a methacrylic acid-methyl methacrylate polymer, or can also be processed into sustained release formulations by being coated with ethyl cellulose, carnauba wax, hydrogenated oil, or the like. In addition, in order to produce a capsule agent, a powder agent or a granule is filled into a hard capsule, or the active ingredient is directly coated with gelatin, or is first dissolved in glycerin, polyethylene glycol, sesame oil, olive oil or the like, and is then coated with gelatin, so as to prepare a soft capsule.

In order to produce an injection, the active ingredient is dissolved in distilled water for injection, as necessary, together with a pH adjuster such as hydrochloric acid, sodium hydroxide, lactose, lactic acid, sodium, sodium monohydrogen phosphate or sodium dihydrogen phosphate, and a tonicity agent such as sodium chloride or glucose, and thereafter, the obtained solution is subjected to aseptic filtration, and is then filled into an ampule. Otherwise, mannitol, dextrin, cyclodextrin, gelatin or the like is further added to the resulting solution, followed by vacuum freeze drying, so as to prepare an injection that is soluble at the time of use. Alternatively, lecithin, polysorbate 80, polyoxyethylene hydrogenated castor oil, or the like is added to the active ingredient, and the obtained mixture is then emulsified in water, so as to prepare an emulsion for injection.

In order to produce a rectal administration agent, the active ingredient, together with a suppository base agent such as cacao butter, fatty acid tri-, di- and mono-glyceride, or polyethylene glycol, is humidified and is dissolved, and the resultant is then poured into a mold, followed by cooling. Otherwise, the active ingredient may be dissolved in polyethylene glycol, soybean oil, or the like, and may be then coated with a gelatin film, etc.

The applied dose and the number of doses of the pharmaceutical composition according to the present embodiment are not particularly limited. The applied dose and the number of doses can be appropriately selected according to the judgment of a doctor or a pharmacist, depending on conditions such as the purpose of preventing and/or treating deterioration and/or progression of a treatment target disease, the type of the disease, and the body weight and age of a patient.

Generally, the dose applied for an adult per day by oral administration is approximately 0.01 to 1,000 mg (the weight of the active ingredient), and this dose can be administered once or divided over several administrations per day, or every several days. In the case of using the pharmaceutical composition as an injection, the injection is desirably administered to an adult continuously or intermittently at a daily dose of 0.001 to 100 mg (the weight of the active ingredient).

Another form of the pharmaceutical composition according to the present embodiment may be a cytotoxic cell such as a T cell that expresses the antibody according to the present embodiment or an antigen-binding fragment thereof on the cell surface thereof. Chimeric antigen receptor-T cell (CAR-T) therapy is a therapy, in which a fusion gene (chimeric antigen receptor gene) of an antigen-binding site of an antibody and a part of a T cell receptor is expressed in T cells, and the T cells are then transferred into the body of a cancer patient, so that the transferred T cells specifically attack cancer cells and provide antitumor activity thereon. By using the gene encoding the antibody according to the present embodiment or an antigen-binding fragment thereof as a component of the above-described chimeric antigen receptor gene to construct the expressing T cells, the CAR-T therapy that specifically attacks a tumor expressing CADM1 molecules, for example, adult T-cell leukemia/lymphoma, can be constructed.

In addition, the antibody according to the present embodiment can also be utilized as a ligand for nanoparticles such as gold nanoparticles as typical examples, or for DDS carriers such as micelles and liposomes.

A fifth embodiment of the present invention relates to a method for preventing and/or treating cancer (for example, adult T-cell leukemia/lymphoma, etc.), comprising administering the pharmaceutical composition according to the present embodiment to a patient (hereinafter also referred to as the preventive or therapeutic method according to the present embodiment").

Herein, the term "treatment" is used to mean prevention or alleviation of the progression and deterioration of the pathologic conditions of a patient who has already been affected with a cancer such as adult T-cell leukemia/lymphoma, by which the progression and deterioration of the cancer is prevented or alleviated.

On the other hand, the term "prevention" is used to mean that the onset of a cancer to be treated, such as adult T-cell leukemia/lymphoma, is inhibited in advance in a being that will be likely to be affected with the cancer for the purpose of inhibiting the onset of the cancer in advance. Furthermore, the measures for inhibiting the recurrence of a cancer after the treatment thereof is also included in the "prevention."

Further, the target of the treatment and the prevention is not limited to a human, and may also be a mammal other than the human. Examples of the mammal may include mice, rats, dogs, and cats, as well as livestock animals such as bovines, horses and sheep, and primates such as monkeys, chimpanzees and gorillas. The target of the treatment and the prevention is particularly preferably a human.

A sixth embodiment of the present invention relates to a method for diagnosing or assisting the diagnosis of adult T-cell leukemia/lymphoma, using the anti-CADM1 antibody according to the present embodiment. The anti-CADM1 antibody according to the present embodiment can specifically bind to a CADM1 molecule, and thus, by labeling the anti-CADM1 antibody with a fluorescent substance, a radioisotope, an enzyme, etc., adult T-cell leukemia/lymphoma cells and the like that express the CADM1 molecules can be detected. Examples of the detection method may include an immunostaining method, a flow cytometric method, a Western blotting method, an ELISA method, a RIA method, a CLIA method, and a PET method. It is possible to directly detect cancer cells in a body, or to observe the expression level of CADM1 in a patient sample. Furthermore, the expression level of CADM1 in a case can be estimated in advance by a method using the anti-CADM1 antibody according to the present embodiment, so that the therapeutic effects obtained by administration of the pharmaceutical composition according to the present embodiment can be predicted (or the therapeutic effects can be supplementarily predicted).

The disclosures of all publications cited in the present description are incorporated herein by reference in their entirety. In addition, throughout the present description, when the description includes singular terms with the articles "a," "an," and "the," these terms include not only single items but also multiple items, unless otherwise clearly specified from the context that it is not the case.

Hereinafter, the present invention will be further described in the following examples. However, these examples are only illustrative examples of the embodiments of the present invention, and thus, are not intended to limit the scope of the present invention.

EXAMPLES

1. Confirmation of CADM1 Variants Expressed in Adult T-Cell Leukemia/Lymphoma (ATLL) Cells In order to confirm the variants of CADM1 expressed in ATLL cells, total RNA was extracted from ATLL cell lines (ATN1 and TL-Om1) and HTLV-1 (Human T-cell leukemia virus type 1) cell lines (MT-2 and HUT102). ATN1 and HUT102 were transferred by Japanese Foundation for Cancer Research. TL-Om1 was provided by Professor Kazuo Sugamura (current Emeritus Professor) of Tohoku University. In addition, MT-2 was provided by Professor Hiroo Hoshino (current Emeritus Professor) of Gunma University.

For the extraction of total RNA, cell pellets were suspended in TRIzol RNA Isolation Reagents (Invitrogen, Thermo Fisher Scientific) immediately after collection, and the total RNA was obtained by a phenol/chloroform treatment and propanol precipitation. The CADM1 gene region was amplified employing SMARTer RACE 5'/3' Kit (TaKaRa) and using 5' RACE and 3' RACE. The primers used for the 5' RACE/3' RACE are as follows.

```
5' RACE
                                        (SEQ ID NO: 21)
GATTACGCCAAGCTTCTAGATGAAGTACTCTTTCTTTTCTTCGGAGT

TGTTCTGTCCTCCTTCTGC

3' RACE
                                        (SEQ ID NO: 22)
GATTACGCCAAGCTTATGGCGAGTGTAGTGCTGCCGAGCGG
```

The amplified DNA was subjected to agarose gel electrophoresis, and was then subjected to gel cutting and DNA extraction. Thereafter, CADM1 was cloned using In-Fusion HD cloning kit (TaKaRa), and the amino acid sequence thereof was then determined by sequence analysis.

From the determined amino acid sequence of CADM1, it was confirmed that the full-length extracellular domain of CADM1 was not expressed in the ATLL cell lines and the HTLV-1 cell lines, and that only an exon 9-10-deficient variant (Δ9-10) and an exon 10-deficient variant (Δ10) were expressed therein (FIG. 1). Similar results were reported by Nakahata et al. (Nakahata et al., Haematologica. 2020 Feb. 13: haematol. 2019. 234096.).

2. Production of Immunizing Antigen

An antigen was designed under the conditions that the antigen is a variant that has been confirmed to be expressed in ATLL, that the antigen comprises an antigen that imitates a higher-order structure on the cell, and that the antigen comprises multiple variants. As a result, 4 types of proteins including monomeric CADM1 and Fc-fused CADM1 capable of forming a dimer were mixed with one another, and the mixture was used as an immunizing antigen (FIG. 2). More specifically, the DNA sequences encoding the amino acid sequences of, a Δ9-10 variant of a CADM1 extracellular domain (hereafter referred to as "CADM1ecΔ9-10"), a 410 variant of a CADM1 extracellular domain (hereafter referred to as "CADM1ecΔ10"), a Δ9-10 Fc variant formed by fusing human Fc with a CADM1 extracellular domain (hereinafter referred to as "CADM1FcΔ9-10"), and a 410 Fc variant formed by fusing human Fc with a CADM1 extracellular domain (hereinafter referred to as "CADM1FcΔ10"), as shown below, were amplified by a PCR method, and were then inserted into a pcDNA3.4 TOPO vector (Thermo Fisher) using NEBuilder HiFi DNA assembly.

```
CADM1ec Δ9-10
                                        (SEQ ID NO: 9)
QNLFTKDVTVIEGEVATISCQVNKSDDSVIQLLNPNRQTIYFRDFRP

LKDSRFQLLNFSSSELKVSLTNVSISDEGRYFCQLYTDPPQESYTTI

TVLVPPRNLMIDIQKDTAVEGEEIEVNCTAMASKPATTIRWFKGNTE

LKGKSEVEEWSDMYTVTSQLMLKVHKEDDGVPVICQVEHPAVTGNLQ

TQRYLEVQYKPQVHIQMTYPLQGLTREGDALELTCEAIGKPQPVMVT

WVRVDDEMPQHAVLSGPNLFINNLNKTDNGTYRCEASNIVGKAHSDY
```

-continued

```
MLYVYDPPTTIPPPTTTTTTTTTTTTTILTIITDSRAGEEGSIRAAA

AEQKLISEEDLNSAVDHHHHHH

CADM1ec Δ10
                                        (SEQ ID NO: 10)
QNLFTKDVTVIEGEVATISCQVNKSDDSVIQLLNPNRQTIYFRDFRP

LKDSRFQLLNFSSSELKVSLTNVSISDEGRYFCQLYTDPPQESYTTI

TVLVPPRNLMIDIQKDTAVEGEEIEVNCTAMASKPATTIRWFKGNTE

LKGKSEVEEWSDMYTVTSQLMLKVHKEDDGVPVICQVEHPAVTGNLQ

TQRYLEVQYKPQVHIQMTYPLQGLTREGDALELTCEAIGKPQPVMVT

WVRVDDEMPQHAVLSGPNLFINNLNKTDNGTYRCESNIVGKAHSDYM

LYVYDPPTTIPPPTTTTTTTTTTTTTILTIITDTTATTEPAVHDSRA

GEEGSIRAHHHHHH

CADM1Fc Δ9-10
                                        (SEQ ID NO: 11)
NLFTKDVTVIEGEVATISCQVNKSDDSVIQLLNPNRQTIYFRDFRPL

KDSRFQLLNFSSSELKVSLTNVSISDEGRYFCQLYTDPPQESYTTIT

VLVPPRNLMIDIQKDTAVEGEEIEVNCTAMASKPATTIRWFKGNTEL

KGKSEVEEWSDMYTVTSQLMLKVHKEDDGVPVICQVEHPAVTGNLQT

QRYLEVQYKPQVHIQMTYPLQGLTREGDALELTCEAIGKPQPVMVTW

VRVDDEMPQHAVLSGPNLFINNLNKTDNGTYRCEASNIVGKAHSDYM

LYVYDPPTTIPPPTTTTTTTTTTTTTILTIITDTTATTEPAVHGLTQ

LPNSAEELDSEDLSDSRAGEEGSIRAAAAEPKSCDKTHTCPPCPAPE

LLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKA

LPAPIEKTISKAKGQPREPQVYTLPPSRDELTKNQVSLTCLVKGFYP

SDIAVEWESNGQPENNYKTTPPVLDSDGSFFLYSKLTVDKSRWQQGN

VFSCSVMHEALHNHYTQKSLSLSPGK

CADM1Fc Δ10
                                        (SEQ ID NO: 12)
QNLFTKDVTVIEGEVATISCQVNKSDDSVIQLLNPNRQTIYFRDFRP

LKDSRFQLLNFSSSELKVSLTNVSISDEGRYFCQLYTDPPQESYTTI

TVLVPPRNLMIDIQKDTAVEGEEIEVNCTAMASKPATTIRWFKGNTE

LKGKSEVEEWSDMYTVTSQLMLKVHKEDDGVPVICQVEHPAVTGNLQ

TQRYLEVQYKPQVHIQMTYPLQGLTREGDALELTCEAIGKPQPVMVT

WVRVDDEMPQHAVLSGPNLFINNLNKTDNGTYRCEASNIVGKAHSDY

MLYVYDPPTTIPPPTTTTTTTTTTTTTILTIITDTTATTEPAVHDSR

AGEEGSIRAAAAEPKSCDKTHTCPPCPAPELLGGPSVFLFPPKPKDT

LMISRTPEVTCVVVDVSHEDPEVKFNWYVDGVEVHNAKTKPREEQYN

STYRVVSVLTVLHQDWLNGKEYKCKVSNKALPAPIEKTISKAKGQPR

EPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQ

KSLSLSPGK
```

Employing Expi293 Expression system (Thermo Fisher), the thus produced vector was allowed to express in a culture supernatant, using human expi293 cells. Four types of CADM1 variants were purified from the culture supernatant by metal affinity chromatography, followed by final purification by size exclusion chromatography. The thus purified 4 types of CADM1 variants, namely, CADM1ecΔ9-10, CADM1ecΔ10, CADM1FcΔ9-10 and CADM1FcΔ10 were mixed with one another, and thereafter, the thus obtained sample was concentrated to 0.7 mg/ml (1 ml) using Amicon Ultra 30K (Merck), so as to prepare an immunizing antigen.

3. Production of Monoclonal Antibody Recognizing CADM1

3-1. Cloning of Hybridomas Producing Anti-CADM1 Antibody

A monoclonal antibody was produced according to an ordinary method (Kohler and Milstein, Nature, 256, 495-497, 1975). The immunizing antigen prepared in the above 2 was mixed with a Freund's adjuvant, and WKAH/Hkm Slc rats (Japan SLC) were then immunized with the obtained mixture, a total of three times every two weeks. Thereafter, splenic cells were prepared from the rats, and the prepared splenic cells were then fused with myeloma cells to prepare hybridomas. Using the culture supernatant of these hybridomas, only those producing anti-CADM1 monoclonal antibodies were selected by a flow cytometric method (clone name: YTH-W-2C2).

3-2. Cloning of Variable Regions of Anti-CADM1 Antibody

Immediately after collection of the pellets of YTH-W-2C2 cells, the pellets were suspended in TRIzol RNA Isolation Reagents (1 ml), and total RNA was then obtained by a phenol/chloroform treatment and propanol precipitation. Employing the SMARTer RACE 5'/3' Kit (TaKaRa), a region ranging from the heavy chain variable region of the YTH-W-2C2 antibody to a rat IgG2a heavy chain constant region, and a region ranging from the light chain variable region to a κ light chain constant region, were amplified using 5' RACE (FIG. 3*a*). The amplified DNA was subjected to agarose gel electrophoresis, and was then subjected to gel cutting and DNA extraction. Thereafter, employing the In-Fusion HD cloning kit (TaKaRa), heavy chain and light chain DNAs were each cloned (FIG. 3*b*). Subsequently, sequence analysis was performed to determine the amino acid sequence of the heavy chain (SEQ ID NO: 13; the signal sequence is shown in SEQ ID NO: No. 14 and the amino acid sequence of the constant region is shown in in SEQ ID NO: No. 16) and the amino acid sequence of the light chain (SEQ ID NO: 17; the signal sequence is shown in SEQ ID NO: No. 18 and the amino acid sequence of the constant region in SEQ ID NO: No. 20). The amino acid sequences of the variable regions of the heavy and light chains are shown below.

```
Amino acid sequence of heavy chain variable
region of YTH-W-2C2 antibody
                                (SEQ ID NO: 15)
QVQLQQSGAELAKPGSSVKISCKASGYTFSNYDISWIKQTTGQGLDY

IGYIHTGSGGTYYNEKFKGKATLTVDKSSSTAFMQLSSLTPEDTAVY

YCARTPYVYYGSGYFDFWGPGTMVTVSS
```

```
Amino acid sequence of light chain variable
region of YTH-W-2C2 antibody
                                (SEQ ID NO: 19)
DIVMTQSPSSLAVSAGETVTINCKSSQSLLYSGNQKNYLAWYQQKPG

QSPKLLIYWASTRQSGVPDRFIGSGSGTDFTLTISSVQAEDLAIYYC

QQYYDTPDTFGAGTKLELK
```

From the results of the aforementioned analysis of the amino acid sequences of the heavy chain and light chain of the YTH-W-2C2 antibody, it became clear that, with regard to the amino acid sequences of the CDR regions defined by Kabat et al., the CDR1, CDR2 and CDR3 of the heavy chain are the amino acid sequences as set forth in SEQ ID NO: 1, SEQ ID NO: 2 and SEQ ID NO: 3, respectively, and the CDR1, CDR2 and CDR3 of the light chain are the amino acid sequences as set forth in SEQ ID NO: 4, SEQ ID NO: 5 and SEQ ID NO: 6, respectively. Moreover, it also became clear that, with regard to the amino acid sequences of the CDR regions defined by Chothia et al., the CDR1, CDR2 and CDR3 of the heavy chain are the amino acid sequences as set forth in SEQ ID NO: 7, SEQ ID NO: 8 and SEQ ID NO: 3, respectively, and the CDR1, CDR2 and CDR3 of the light chain are the amino acid sequences as set forth in SEQ ID NO: 4, SEQ ID NO: 5 and SEQ ID NO: 6, respectively.

It is to be noted that ab Ysis (http://www.abysis.org/abysis/index.html) was used for the CDR sequence analyses by the definitions of Kabat and Chothia.

3-3. Production of YTH-W-2C2 Rat Antibody and Chimeric Antibody

The cloned heavy chain and light chain signal sequence-coding sequences and variable region amino acid-coding sequence of a YTH-W-2C2 antibody were introduced into a pcDNA3.4topo expression plasmid. In order to produce a YTH-W-2C2 rat antibody, the cloned heavy chain and light chain full-length DNA sequences ranging from the signal sequence to the constant region were introduced into the pcDNA3.4topo plasmid. In addition, in order to produce a chimeric antibody (a chimeric antibody of the variable region of the YTH-W-2C2 antibody and the constant region of human IgG; hereinafter also referred to as a "YTH-W-2C2 chimeric antibody"), a DNA sequence formed by transplanting the DNA sequence of the variable region into the constant region of human IGHG1 and IGCκ was introduced into the pcDNA3.4topo plasmid (FIG. 4*a*). The expression plasmid was introduced into CHO cells, so that the antibodies were allowed to express in the supernatant of the medium. The medium supernatant obtained after the culture for 10 to 14 days was separated into a cellular component and a supernatant by centrifugation, and was then filtrated though a filter. The YTH-W-2C2 rat antibody was purified using a Protein G column, and the chimeric antibody was purified using a Protein A column (FIG. 4*b*). Thereafter, YTH-W-2C2 rat antibody and the YTH-W-2C2 chimeric antibody were dialyzed against a phosphate buffer, and the final purification was then carried out by size exclusion chromatography (FIG. 4*c*).

4. Studies of Binding Ability of Anti-CADM1 Antibody (YTH-W-2C2 Chimeric Antibody) to CADM1 Monomer and CADM1 Dimer CADM1 has been known to form a dimer on cells (Shingai et al., J Biol Chem. 278: 35421-35427, 2003.) Hence, in order to evaluate the binding affinity of the YTH-W-2C2 chimeric antibody to the antigens (ecΔ9-10, ecΔ10, dimerized FcΔ9-10, and dimerized FcΔ10; see FIG.

2) that were used to immunize rats during antibody production, surface plasmon resonance (SPR) analysis was performed using Biacore 8K.

The antibody was diluted with a phosphate buffered saline (PBS) at a concentration of 1 mg/ml, and was then immobilized as a ligand on a sensor chip CM5 by an amine coupling method. As analytes, samples obtained by serial dilution of Fc full, FcΔ10 and FcΔ9-10 (from 1.56 nM to 50 nM), and ec full, ecΔ10 and ecΔ9-10 (from 6.25 nM to 200 nM) were used, and the association rate constant ($k_a$), dissociation rate constant ($k_d$) and dissociation constant ($K_D$) were calculated according to a multi-cycle kinetic analysis method. The results of the analysis are summarized in Table 1.

TABLE 1

| CADM1 | ka(1/MS) | $k_d$(1/s) | $K_D$(M) |
|---|---|---|---|
| Fc full | $2.2 \times 10^5 \pm 0.5 \times 10^5$ | $1.4 \times 10^{-4} \pm 1.0 \times 10^{-4}$ | $7.7 \times 10^{-10} \pm 7.5 \times 10^{-10}$ |
| Fc10 | $2.4 \times 10^5 \pm 0.1 \times 10^5$ | $1.5 \times 10^{-4} \pm 0.8 \times 10^{-4}$ | $6.4 \times 10^{-10} \pm 3.8 \times 10^{-10}$ |
| Fc9-10 | $2. \times 10^5 \pm 0.8 \times 10^5$ | $1.4 \times 10^{-4} \pm 1.0 \times 10^{-4}$ | $4.6 \times 10^{-10} \pm 2.1 \times 10^{-10}$ |
| ec full | $8.0 \times 10^4 \pm 1.8 \times 10^4$ | $1.9 \times 10^{-2} \pm 0.4 \times 10^4$ | $2.5 \times 10^{-7} \pm 0.1 \times 10^{-7}$ |
| ec10 | $9.4 \times 10^4 \pm 1.0 \times 10^4$ | $1.9 \times 10^{-2} \pm 0.2 \times 10^{-2}$ | $2.1 \times 10^{-7} \pm 0.4 \times 10^{-7}$ |
| ec9-10 | $1.5 \times 10^5 \pm 0.7 \times 10^5$ | $1.7 \times 10^{-2} \pm 0.3 \times 10^{-2}$ | $1.3 \times 10^{-7} \pm 0.6 \times 10^{-7}$ |

No differences were observed in the binding affinity (dissociation constant $K_D$) and the kinetic parameters (binding rate constant $k_a$ and dissociation rate constant $k_d$) among the full-length CADM1 and the Δ10 and Δ9-10 variants. However, when the monomers (ec full, ecΔ10, and ecΔ9-10) were compared with the dimers (Fc full, FcΔ10, and FcΔ9-10), it became clear that the dissociation ($k_d$) became significantly slow in the dimeric CADM1, and that YTH-W-2C2 binds to the dimers with higher binding affinity. The aforementioned results suggested that YTH-W-2C2 binds to the full-length CADM1 and the Δ10 and Δ9-10 variants with equal affinity, and that it binds to the dimeric CADM1 with higher affinity than to the monomeric CADM1.

It has been reported that the selective splicing of CADM1 or the cleavage of CADM1 on the membrane results in the appearance of a soluble form (sCADM1) of the CADM1 extracellular domain. It has been reported that this sCADM1 is elevated in the plasma of ATL patients from a smoldering form to an acute form. It has been demonstrated that the sCADM1 is elevated up to about 1-10 μg/ml at maximum in the aggressive-type lymphoma, acute-type ATL, which has the highest blood concentration (Nakahata et al., Haematologica. 2020 Feb. 13: haematol. 2019. 234096.). In addition, in order to analyze the biological functions and adhesion-associated affinity of such soluble proteins as CADM1 and another Nectin like molecule (Necl), an analysis has been carried out using CADM1 fused with the Fc domain of the antibody to dimerize the extracellular domain (Shingai et al., J Biol Chem. 278: 35421-35427, 2003: Arase et al., Int Immunol. 17: 1227-1237, 2005; Ito et al., Front Cell Dev Biol. 6: 86, 2018). The aforementioned results suggest that CADM1 needs to be dimerized in order to be active in a solution. As mentioned above, taking into consideration that the concentration of the soluble form sCADM1 in blood is at maximum 1-10 g/ml, namely, at such a low concentration as several-hundred nM order, and thus that the sCADM1 needs to be dimerized in order to function in a solution, it is suggested that the sCADM1 exists as a monomer. Since YTH-W-2C2 exhibits higher binding affinity to a dimerized antigen, it is suggested that the YTH-W-2C2 is likely to bind with higher affinity to dimeric CADM1 on cells, than to sCADM1 in blood, and it is considered that the YTH-W-2C2 can effectively bind to target cells in the development of a treatment method using antibodies, even if the soluble form CADM1 is present in blood.

5. Biological Studies of Anti-CADM1 Antibodies (YTH-W-2C2 Rat Antibody and YTH-W-2C2 Chimeric Antibody)

5-1. Studies of Binding Ability to CADM1 on Cell Surface

CEM (a T cell line derived from a patient with acute T lymphoblastic leukemia; $CADM1^-$), TL-Om1 (a T cell line derived from a patient with ATLL; $CADM1^{++}$), and MT-2 (an HTLV-1-infected, immortalized T cell line; $CADM1^{++}$) were each subjected to cell counting, and three 1.5-mL tubes each containing $5 \times 10^5$ cells were prepared for each cell line.

The following 3 types of antibody solutions that had previously been diluted with FACS buffer (PBS+2% FBS) were prepared:

(a) 10 μg/mL anti-CADM1 antibody (Rat-IgG; YTH-W-2C2 rat antibody);

(b) 10 μg/mL anti-CADM1 antibody (Human-Fc-Rat-IgG; YTH-W-2C2 chimeric antibody); and (c) Isotype control: normal mouse IgG-PE/normal mouse IgG-FITC (10 μg/mL each).

Into the three tubes containing each cell line, the antibody solutions (a), (b) and (c) (100 μL each) were each added, and then, the antibody solution was fully blended by pipetting. Thereafter, the resulting solution was incubated in a dark place at room temperature for 20 minutes. Into each tube, 500 μL of FACS buffer was added, and then, the obtained solution was gently stirred with Vortex for about 2 seconds (washing of the cells). The resulting solution was centrifuged at 1500 rpm at 25° C. for 1 minute, and the supernatant was then removed.

As secondary antibody solutions, the following solutions (d) and (e) were prepared:

(d) Anti-rat-IgG-Alexa546 (Thermo Fisher Scientific) that was 500-fold diluted with FACS buffer; and (e) Anti-human-IgG-Alexa546 (Thermo Fisher Scientific) that was 500-fold diluted with FACS buffer.

The solution (d) (100 μL) was added into the tube of each cell line containing the antibody (a), and the solution (e) (100 L) was added to the tube of each cell line containing the antibody (b). After fully blending by pipetting, the obtained mixture was incubated in a dark place at room temperature for 20 minutes. Thereafter, 500 μL of FACS buffer was added to the tube of each cell line, and then, the obtained solution was gently stirred with Vortex for about 2 seconds (washing of the cells). The resulting solution was centrifuged at 1500 rpm at 25° C. for 1 minute, and the supernatant was then removed. After that, 300 μL of fresh FACS buffer was added again to the tube of each cell line, and then, the obtained mixture was fully blended by pipetting. The reaction mixture was transferred into a tube for a flow cytometer.

Using the flow cytometer Novocyte (ACEA Biosciences, Inc./Agilent Technologies, Inc.), Alexa488/FITC wavelength or Alexa546/PE wavelength was detected. The obtained data were analyzed using NovoExpress (ACEA Biosciences, Inc./Agilent Technologies, Inc.) and FlowJo (FlowJo, LLC/Becton, Dickinson and Company (BD)). The analysis results are shown in FIG. 5. CADM1(−) CEM cells, or the CADM1(+) HTLV-1-infected cell line MT-2 and the CADM1(+) ATL patient-derived cell line TL-Om1 were immunostained using anti-CADM1-Rat-IgG (YTH-W-2C2 rat antibody) or anti-CADM1-Human-Fc-Rat-IgG-IgG (YTH-W-2C2 chimeric antibody) as a primary antibody, and using, respectively, anti-Rat-IgG-Alexa546 or anti-Human-IgG-Alexa546 as a secondary antibody. As a result, it was found that both anti-CADM1-IgGs could detect CADM1 on the MT-2 cell membrane (FIG. 5, center) and the TL-Om1 cell membrane (FIG. 5, right), and that both anti-CADM1-IgGs did not show non-specific binding to the CEM cells (FIG. 5, left).

5-2. Studies of Labeling Conditions for Antibodies (Biotinylation)

5-2-1. Biotinylation of Antibodies

The 3 types of anti-CADM1 antibodies (a YTH-W-2C2 rat antibody, a YTH-W-2C2 chimeric antibody, and IgY (MBL)) were biotinylated by the following method.

First, 50 μL (1 μg/μL) of the antibody and 350 μL of a reaction buffer (100 mM $NaHCO_3$, pH 8.4) were placed in Centricut Ultra-mini (W=50: fraction 50 kDa), and were then centrifuged until about 50 L of the reaction mixture remained in the upper chamber (10,000 g, ~20 min, 4° C.). Thereafter, 350 μL of the reaction buffer was added again, and the obtained mixture was then centrifuged until about 50 μL of the reaction mixture remained (10,000 g, ~20 min, 4° C.). These operations were repeated twice, and 50 μL of the antibody solution was then transferred into a new 1.5-mL tube.

A biotin solution was prepared by dissolving biotin in DMSO (dimethyl sulfoxide) to a concentration of 1 mg/mL, and 2.5 μL of the prepared biotin solution was then added to each antibody solution. The mixture was blended by pipetting, and was then left in a dark place at room temperature for 2 hours.

To each antibody solution added with the biotin solution, 350 μL of PBS was added, and the obtained mixture was then centrifuged until about 50 μL of a liquid remained (10,000 g, ~20 min, 4° C.). These operations were repeated twice. To the biotinylated antibody (50 μL) remaining in the upper chamber, 50 μL of PBS was added, so as to obtain a biotinylated antibody (final concentration: 500 ng/μL).

5-2-2. Verification of Biotinylation According to Flow Cytometric Analysis

CEM cells, TL-Om1 cells, MT-2 cells, and PBMC cells (chronic ATLL patient-derived cell line) were subjected to cell counting, and four 1.5-mL tubes each containing $5\times10^5$ cells were prepared for each cell line.

The following 3 types of antibody solutions that had previously been diluted with a FACS buffer (PBS+2% FBS) were prepared:

(a) 10 μg/mL biotinylated anti-CADM1 antibody (Rat-IgG; YTH-W-2C2 rat antibody);

(b) 10 μg/mL biotinylated anti-CADM1 antibody (Human-Fc-Rat-IgG; YTH-W-2C2 chimeric antibody);

(c) 10 μg/mL biotinylated anti-CADM1 antibody (IgY); and (d) without a primary antibody (only the FACS buffer).

Into the four tubes of each cell line, the antibody solutions (a), (b) and (c) or the FACS buffer (d) (100 μL each) were each added, and then, the obtained solution was fully blended by pipetting. Thereafter, the resultant was incubated in a dark place at room temperature for 20 minutes. Into each tube, 500 μL of the FACS buffer was added, and then, the obtained solution was gently stirred with Vortex for about 2 seconds (washing of the cells). The resulting solution was centrifuged at 1500 rpm at 25° C. for 1 minute, and the supernatant was then removed. After that, 100 μL each of Streptavidin-PE solution (100-fold diluted with the FACS buffer, BioLegend Inc.) was added to all of the tubes, and thereafter, the obtained mixture was fully blended by pipetting and was then incubated in a dark place at room temperature for 20 minutes. To each tube, 500 μL of the FACS buffer was added, and the obtained solution was gently stirred with Vortex for about 2 seconds (washing of the cells). Thereafter, the resulting solution was centrifuged at 1500 rpm at 25° C. for 1 minute, and the supernatant was then removed. After that, 300 μL of a fresh FACS buffer was added again to the tube of each cell line, and then, the obtained mixture was fully blended by pipetting. The reaction mixture was transferred into a tube for a flow cytometer.

Using the flow cytometer Novocyte (ACEA Biosciences, Inc./Agilent Technologies, Inc.), PE wavelength was detected. The obtained data were analyzed using NovoExpress (ACEA Biosciences, Inc./Agilent Technologies, Inc.) and FlowJo (FlowJo, LLC/Becton, Dickinson and Company (BD)). The analysis results are shown in FIG. 6.

When the YTH-W-2C2 rat antibody and the YTH-W-2C2 chimeric antibody according to the present invention were biotinylated, their binding affinity to CADM1-expressing cells was not as strong as that of biotinylated IgY (MBL). On the other hand, since clear binding was confirmed from the two-step labeling (FIG. 5) and the direct labeling (FIG. 7), it is said that labeling and detection methods other than biotinylation are suitable for these antibodies.

5-3. Studies of Labeling Conditions for Antibodies (Alexa488 Direct Labeling)

Two types of anti-CADM1 antibodies (a YTH-W-2C2 rat antibody and a YTH-W-2C2 chimeric antibody) were labeled with Alexa488 (Thermo Fisher Scientific). Subsequently, CEM cells, TL-Om1 cells, MT-2 cells and PBMC cells (derived from chronic ATLL patients) were subjected to cell counting, and four 1.5-mL tubes each containing $5\times10^5$ cells were prepared for each cell line.

The following 3 types of antibody solutions that had previously been diluted with a FACS buffer (PBS+2% FBS) were prepared:

(a) 10 μg/mL Alexa488-anti-CADM1 antibody (Rat-IgG; YTH-W-2C2 rat antibody);

(b) 10 μg/mL Alexa488-anti-CADM1 antibody (Human-Fc-Rat-IgG; YTH-W-2C2 chimeric antibody);

(c) 10 μg/mL PE-anti-CADM1 antibody (IgY); and (d) Isotype control: normal mouse IgG-PE/normal mouse IgG-FITC (10 μg/mL each).

Into the four tubes of each cell line, the antibody solutions (a), (b), (c) and (d) were each added (100 μL each), and then, the obtained solution was fully blended by pipetting. Thereafter, the resultant was incubated in a dark place at room temperature for 20 minutes. Into each tube, 500 μL of the FACS buffer was added, and then, the obtained solution was gently stirred with Vortex for about 2 seconds (washing of the cells). The resulting solution was centrifuged at 1500 rpm at 25° C. for 1 minute, and the supernatant was then removed. After that, 300 μL of a fresh FACS buffer was added again to the tube of each cell line, and then, the obtained mixture was fully blended by pipetting. The reaction mixture was transferred into a tube for a flow cytometer.

Using the flow cytometer Novocyte (ACEA Biosciences, Inc./Agilent Technologies, Inc.), Alexa488/FITC wavelength or PE wavelength was detected. The obtained data were analyzed using NovoExpress (ACEA Biosciences, Inc./Agilent Technologies, Inc.) and FlowJo (FlowJo, LLC/Becton, Dickinson and Company (BD)). The analysis results are shown in FIG. 7.

The YTH-W-2C2 rat antibody and the YTH-W-2C2 chimeric antibody according to the present invention exhibited binding affinity to CADM1 at a level similar to (TL-Om1) or higher than (MT-2 and PBMC) the existing PE-IgYs according to direct fluorescence labeling. In particular, the present YTH-W-2C2 rat antibody and the present YTH-W-2C2 chimeric antibody exhibited higher detection ability than PE-IgYs to CADM1 on the surface of tumor T cells derived from patients with chronic-type ATL.

5-4. Confirmation of Internalization of CADM1/CADM1 Antibody Conjugate into Cells MT-2 cells were subjected to cell counting, and were then suspended in RPM1 (10% FBS) to a concentration of $5\times10^5$ cells/1 mL/well, and were then seeded on 8 wells of a 12-well plate. The cells contained in 2 wells were transferred into two 1.5-mL tubes (1 well/1 tube), and the remaining cell plate was placed in an incubator, followed by initiation of the culture (37° C., 5% $CO_2$). The tube containing the cells was centrifuged at 1500 rpm at 25° C. for 1 minute, and the supernatant was then removed.

The following antibody solutions that had previously been diluted with a FACS buffer (PBS+2% FBS) were placed in each tube (100 μL each), and thereafter, the antibody solution was fully blended by pipetting, and was then incubated in a dark place at room temperature for 20 minutes:

(a) 10 μg/mL anti-CADM1 antibody (Rat-IgG; YTH-W-2C2 rat antibody); and (b) 10 μg/mL anti-CADM1 antibody (Human-Fc-Rat-IgG; YTH-W-2C2 chimeric antibody).

Subsequently, 500 μL of the FACS buffer was added to each tube, and then, the obtained solution was gently stirred with Vortex for about 2 seconds (washing of the cells). The resulting solution was centrifuged at 1500 rpm at 25° C. for 1 minute, and the supernatant was then removed.

The cells in each tube were suspended in 1 mL of RPMI (10% FBS), and the obtained suspension was then returned to the 8 wells of the plate, in which the cells had been first seeded (6-hour internalization sample), and thereafter, the culture was continued. The operations after the above-described seeding were carried out at 2 hours after the first seeding (4-hour internalization sample), at 4 hours after the first seeding (2-hour internalization sample), and at 6 hours after the first seeding (0-hour internalization sample). Immediately after the preparation of the 0-hour internalization sample, the cells in other wells that had been continuously cultured were also each transferred into 1.5-mL tubes, and were then centrifuged at 1500 rpm at 25° C. for 1 minute, and thereafter, the supernatant was removed.

As secondary antibodies, the following antibody solutions were prepared, and thereafter, the antibody solution (c) was prepared in the tube (a), and 100 μL each of the antibody solution (d) was added into the tube (b), and after fully blending by pipetting, the obtained mixture was incubated in a dark place at room temperature for 20 minutes:

(c) Anti-Rat-IgG (YTH-W-2C2 rat antibody)-Alexa546 (Thermo Fisher Scientific) that was 500-fold diluted with the FACS buffer; and (d) Anti-Human-IgG (YTH-W-2C2 chimeric antibody)-Alexa488 (Thermo Fisher Scientific) that was 500-fold diluted with the FACS buffer.

Thereafter, 500 μL of the FACS buffer was added to each tube, and then, the obtained solution was gently stirred with Vortex for about 2 seconds (washing of the cells). The resulting solution was centrifuged at 1500 rpm at 25° C. for 1 minute, and the supernatant was then removed. After that, 300 μL of a fresh FACS buffer was added again to the tube of each cell line, and then, the obtained mixture was fully blended by pipetting. The reaction mixture was transferred into a tube for a flow cytometer.

Using the flow cytometer Novocyte (ACEA Biosciences, Inc./Agilent Technologies, Inc.), Alexa488 wavelength or Alexa546 wavelength was detected. The obtained data were analyzed using NovoExpress (ACEA Biosciences, Inc./Agilent Technologies, Inc.) and FlowJo (FlowJo, LLC/Becton, Dickinson and Company (BD)).

After completion of the flow cytometry, the residual cell solution was attached onto a glass slide with Cytospin (800 rpm, 3 minutes, and room temperature), and was immobilized with 4% PFA for 10 minutes without excessive drying. After washing the glass slide with PBS three times, it was sealed with a mounting solution (80% glycerol+DAPI+fading inhibitor), and was then observed under a fluorescence microscope (Olympus IX70, OLYMPUS Corp.). The analysis results are shown in FIG. 8.

In studies using a flow cytometer, it was found that the YTH-W-2C2 rat antibody and the YTH-W-2C2 chimeric antibody according to the present invention bound to CADM1 on the surface of MT-2 cells, and 2 hours later, the fluorescence signals were attenuated. In addition, when these MT-2 cells were observed under a fluorescence microscope, the conjugates of the CADM1 and the antibodies, which had been scattered in the form of granules on the surface of the MT-2 cells at 0 hour, disappeared after 2 hours, except for the adhesion sites between the cells. Accordingly, it is considered that both the YTH-W-2C2 rat antibody and the YTH-W-2C2 chimeric antibody were internalized in the cells in the state of conjugates bound to the CADM1.

Next, studies were conducted using CEM cells that were allowed to overexpress CADM1. CEM/hCADM1 cells, in which the CEM cells were allowed to overexpress CADM1, were reacted with anti-CADM1-Human-Fc-Rat-IgG (YTH-W-2C2 chimeric antibody) at room temperature for 20 minutes, and the antibody was then removed by washing. Thereafter, the cells were cultured in an RPMI+10% FBS medium at 37° C. for 0, 2 and 4 hours under 5% $CO_2$ conditions, so as to allow internalization of the CADM1 antibody (anti-CADM1-Human-Fc-Rat-IgG)-CADM1 conjugate. Thereafter, the cells were reacted with a secondary antibody (anti-Human-IgG-Alexa546) at room temperature for 20 minutes, so as to detect the CADM1 antibody-CADM1 conjugate on the cell surface. As a negative control, the same operations were performed on CEM/control cells (vector control CEM cells). The analysis results are shown in FIG. 9. In the results of the flow cytometric analysis (FIG. 9, left), the amount of the CADM1 antibody-CADM1 conjugate in the CEM/hCADM1 cells at 2 hours and 4 hours after the culture was decreased, compared with that at 0 hour after the culture. In addition, the intracellular localization of the CADM1 antibody-CADM1 conjugate (red) and that of the lysosome (green) at individual time points were observed under a fluorescence microscope. As a result, it was found that the CADM1 antibody-CADM1 conjugate, which had been localized on the cell surface at 0 hour after the culture, was localized as a mass in the vicinity of the lysosomes at 2 hours after the culture, and was further co-localized with the lysosome at 4 hours after the culture. From these results, it was suggested that the anti-CADM1-Human-Fc-Rat-IgG is internalized when it binds to CADM1 on the cell surface, and is further incorporated into the lysosome and degraded, indicating the usefulness of the antibody-drug conjugate (ADC). No signals were detected in the CEM/control cells by the anti-CADM1-Human-Fc-Rat-IgG, so that it was confirmed that the anti-CADM1-Human-Fc-Rat-IgG specifically binds to the CADM1 on the cell surface.

Furthermore, these cells (the cells shown in FIG. 9 that were subjected to fluorescence microscopic observation) were observed using a confocal laser microscope. As a result, it was found that, even in the 2D images, the CADM1/CADM1 antibody conjugates (red) were localized near the lysosomes (green) as the time elapsed, and that only the signals of the red were decreased 4 hours later (FIG. 10). These results demonstrated that the CADM1/CADM1 antibody conjugates were incorporated into the lysosomes and were rapidly degraded.

5-5. Production of ADC (Antibody Drug Conjugate) and Influence of ADC on Cells

MMAE (Monomethyl auristatin E) was added to anti-CADM1-Human-Fc-Rat-IgG to produce ADC, and the effects of the ADC specific to CADM1(+) cells were then studied. CEM/hCADM1 cells (CADM1-overexpressing CEM cells), ATL patient-derived cell lines (TL-Om1, MT-1 and ATN-1), and an HTLV-1-infected cell line (MT-2) were used as CADM1(+) cells. CEM/control cells (vector control CEM cells) and untreated CEM cells were used as CEM(−) cells. To the culture solutions of these cells, PBS, MMAE, anti-CADM1-Human-Fc-Rat-IgG alone, and anti-CADM1-Human-Fc-Rat-IgG+MMAE (ADC) were added, and thereafter, cell viability was detected at 0, 2 and 4 days after the addition according to WST8 assay. As a result, when compared with PBS (untreated) (○ (white circles) in the graph of FIG. 11), the treatment with anti-CADM1-Human-Fc-Rat-IgG alone did not affect the cell proliferative ability of all of the cell lines (□ (white squares) in the graph of FIG. 11), while the MMAE treatment induced cell death non-specifically (● (black circles) in the graph of FIG. 11). On the other hand, in the case of the anti-CADM1-IgG+MMAE (ADC) treatment, a significant decrease in cell proliferative ability was observed only in the CADM1(+) cells (■ (gray squares) in the graph of FIG. 11). From these results, it was confirmed that the ADC with anti-CADM1-Human chimera-IgG is specifically incorporated only in the CADM1(+) cells and induces cell death.

Next, the effects of the anti-CADM1-Human-Fc-Rat-IgG+MMAE (ADC) were examined using fresh ATL cells derived from patients with chronic type ATL. Peripheral blood mononuclear cells (PBMCs) were isolated from the blood of patients with chronic ATL, and were then cultured in an RPMI+10% FBS+IL-2 (100 ng/mL) culture medium supplemented with PBS, an anti-CADM1-Human-Fc-Rat-IgG antibody alone (150 nM), or anti-CADM1-Human-Fc-Rat-IgG+MMAE (ADC) (150 nM), under conditions of 37° C. and 5% $CO_2$. Seven days after initiation of the culture, the PBMCs were stained with anti-CADM1-PE, CD7-FITC, CD4-APC, and PI, and were then compared with PI(−)/CD4+ cells in terms of the expression patterns of CD7 and CADM1 (HAS-Flow method; see Kobayashi et al., Clin Cancer Res; 20(11): 2851-2861, 2014., DOI: 10.1158/1078-0432.CCR-13-3169, etc.). According to the HAS-Flow method, CD7(+)/CADM1(−): non-infected cells, CD7(+)/CADM1(+): HTLV1-infected cells, and CD7(−)/CADM1(+): ATL tumor cells, were separated. As a result, when compared with the PBS-treated cells, the HAS-Flow pattern was not changed by the anti-CADM1-Human-Fc-Rat-IgG antibody treatment alone, whereas by the CADM1-Human-Fc-Rat-IgG+MMAE (ADC) treatment, the population of the CD7(−)/CADM1(+): ATL tumor cells was specifically decreased and the percentage of the CD7(+)/CADM1(−): non-infected cells was relatively increased (FIG. 12, upper view).

Moreover, when a comparison was made in terms of the percentage of $CD4^+$ T cells in the PI(−) cell population, the percentage of $CD4^+$ T cells was significantly reduced by the anti-CADM1-Human-Fc-Rat-IgG+MMAE (ADC) treatment, and a decrease in the tumorized ATL cell population was observed (FIG. 12, lower view). From the aforementioned results, it was confirmed that the ADC with the present antibody specifically removes only the CADM1-overexpressing ATL cells and does not affect non-infected T cells in the PBMCs of ATL patients comprising various types of cells.

5-6. Confirmation of ADCC Action by Anti-CADM1 Antibody

Normal human peripheral blood mononuclear cells (PBMCs) were used as effector cells. PBMCs were isolated from peripheral blood, using a lymphocyte separation solution, and were then suspended in RPMI (10% FBS, 20 U/mL IL-2) to a cell density of $8\times10^6$ cells/mL. A green fluorescence-labeled CADM1-positive, HTLV-1-infected T cell line (MT-2) was used as target cells, and was then suspended in RPMI (10% FBS, 20 U/mL IL-2) to a cell density of $4\times10^5$ cells/mL. As antibodies added, negative control antibodies (rat IgG, human IgG), positive control antibodies (an anti-HTLV-1 gp46 antibody (LAT-27), humanized LAT-27 (hu-LAT-27)), and anti-CADM1 antibodies (a YTH-W-2C2 rat antibody and a YTH-W-2C2 chimeric antibody) were used, and were each suspended in RPMI (10% FBS, 20 U/mL IL-2) to a concentration of 20 μg/mL. Thereafter, 50 μL of the effector cells, 25 μL of the target cells, and 25 μL of each antibody were seeded in each well of a 96-well U-bottom plate (effector/target ratio=40), and were then cultured for 4 hours (37° C., 5% $CO_2$). After completion of the culture, the cells were fixed with 1% paraformaldehyde, and all cells were then transferred from each well into a tube for flow cytometry. Moreover, $5\times10^3$ standard particles for flow counting (Beckman Coulter, Inc.) were placed in each tube, and the number of surviving target cells was counted by flow cytometry (BD FACSCalibur, BD CELLQuest Pro). From these remaining numbers, the number of injured target cells was calculated.

As a result, it was revealed that both the YTH-W-2C2 rat antibody and the YTH-W-2C2 chimeric antibody according to the present embodiment bind to CADM1 on the surface of MT-2 cells and are able to kill the target MT-2 cells in cooperation with the effector cells (ADCC action) (FIG. 13 and FIG. 14).

From the aforementioned results, it was demonstrated that the anti-CADM1 antibody according to the present embodiment binds to various cell lines and fresh tumor T cells derived from ATLL patients. In addition, in the cell internalization confirmation experiment, it was observed that the anti-CADM1 antibody according to the present embodiment binds to CADM1 on the cell surface and is thereby internalized into cells in the form of a CADM1/CADM1 antibody conjugate, and it could be confirmed that the anti- CADM1 antibody according to the present embodiment is suitable for the treatment of diseases by processing the present anti-CADM1 antibody into ADC, or the like. Furthermore, by direct labeling with a fluorescent dye, the present anti-CADM1 antibody was observed to have a power of detecting CADM1 on the cell surface, which is comparable to that of commercially available PE-anti-CADM1-IgY, and thus, it was demonstrated that the present anti-CADM1 antibody is useful for various diagnoses and medical applications.

INDUSTRIAL APPLICABILITY

The antibody provided by the present invention and an antigen-binding fragment thereof are considered to play an important role in provision of methods for treating diseases such as, for example, ATLL, or the development of therapeutic agents, etc. Therefore, it is expected that the present invention can be utilized in the medical field, the pharmaceutical field, etc.

The invention claimed is:

1. An antibody binding to CADM1 (Cell adhesion molecule 1), wherein the antibody binds to CADM1 on the surface of a cell and induces internalization of the antibody and the CADM1 into the cell, or an antigen-binding fragment thereof, wherein the amino acid sequences of CDRs (complementarity determining regions) 1-3 satisfy either the following (A) or (B), or an antigen-binding fragment thereof:

(A) the antibody has:

heavy chain CDR1 comprising the amino acid sequence as set forth in SEQ ID NO: 1, heavy chain CDR2 comprising the amino acid sequence as set forth in SEQ ID NO: 2, heavy chain CDR3 comprising the amino acid sequence as set forth in SEQ ID NO: 3, light chain CDR1 comprising the amino acid sequence as set forth in SEQ ID NO: 4, light chain CDR2 comprising the amino acid sequence as set forth in SEQ ID NO: 5, and light chain CDR3 comprising the amino acid sequence as set forth in SEQ ID NO: 6; or (B) the antibody has:

heavy chain CDR1 comprising the amino acid sequence as set forth in SEQ ID NO: 7, heavy chain CDR2 comprising the amino acid sequence as set forth in SEQ ID NO: 8, heavy chain CDR3 comprising the amino acid sequence as set forth in SEQ ID NO: 3, light chain CDR1 comprising the amino acid sequence as set forth in SEQ ID NO: 4, light chain CDR2 comprising the amino acid sequence as set forth in SEQ ID NO: 5, and light chain CDR3 comprising the amino acid sequence as set forth in SEQ ID NO: 6.

2. The antibody according to claim 1, wherein the antibody satisfies either the following (a) or (b), or an antigen-binding fragment thereof:

(a) the antibody has a heavy chain variable region comprising the amino acid sequence as set forth in SEQ ID NO: 15, and a light chain variable region comprising the amino acid sequence as set forth in SEQ ID NO: 19; or (b) the antibody has a heavy chain variable region comprising an amino acid sequence having a sequence identity of 90% or more to the amino acid sequence as set forth in SEQ ID NO: 15, and a light chain variable region comprising an amino acid sequence having a sequence identity of 90% or more to the amino acid sequence as set forth in SEQ ID NO: 19.

3. The antibody according to claim 1, wherein the CADM1 is dimerized on the cell surface, or an antigen-binding fragment thereof.

4. The antibody according to claim 1, wherein the antibody is a humanized antibody or a chimeric antibody, or an antigen-binding fragment thereof.

5. The antibody according to claim 1, wherein the antibody is a human antibody, or an antigen-binding fragment thereof.

6. The antibody according to claim 1, wherein a substance having antitumor activity binds to the antibody, or to the antigen-binding fragment thereof.

7. The antigen-binding fragment according to claim 1, wherein the antigen-binding fragment is Fab, Fab', F $(ab')_2$, Fv, a single-chain antibody, scFv, scFv dimer, or dsFv.

8. A pharmaceutical composition, comprising the antibody according to claim 1 or an antigen-binding fragment thereof.

* * * * *

SEQUENCE LISTING

```
<160> NUMBER OF SEQ ID NOS: 22

<210> SEQ ID NO 1
<211> LENGTH: 5
<212> TYPE: PRT
<213> ORGANISM: Rattus rattus

<400> SEQUENCE: 1

Asn Tyr Asp Ile Ser
1               5


<210> SEQ ID NO 2
<211> LENGTH: 17
<212> TYPE: PRT
<213> ORGANISM: Rattus rattus

<400> SEQUENCE: 2

Tyr Ile His Thr Gly Ser Gly Gly Thr Tyr Tyr Asn Glu Lys Phe Lys
1               5                   10                  15

Gly


<210> SEQ ID NO 3
<211> LENGTH: 13
<212> TYPE: PRT
<213> ORGANISM: Rattus rattus

<400> SEQUENCE: 3

Thr Pro Tyr Val Tyr Tyr Gly Ser Gly Tyr Phe Asp Phe
1               5                   10


<210> SEQ ID NO 4
<211> LENGTH: 17
<212> TYPE: PRT
<213> ORGANISM: Rattus rattus

<400> SEQUENCE: 4

Lys Ser Ser Gln Ser Leu Leu Tyr Ser Gly Asn Gln Lys Asn Tyr Leu
1               5                   10                  15

Ala


<210> SEQ ID NO 5
<211> LENGTH: 7
<212> TYPE: PRT
<213> ORGANISM: Rattus rattus

<400> SEQUENCE: 5

Trp Ala Ser Thr Arg Gln Ser
1               5


<210> SEQ ID NO 6
<211> LENGTH: 9
```

<212> TYPE: PRT
<213> ORGANISM: Rattus rattus

<400> SEQUENCE: 6

Gln Gln Tyr Tyr Asp Thr Pro Asp Thr
1 5

<210> SEQ ID NO 7
<211> LENGTH: 7
<212> TYPE: PRT
<213> ORGANISM: Rattus rattus

<400> SEQUENCE: 7

Gly Tyr Thr Phe Ser Asn Tyr
1 5

<210> SEQ ID NO 8
<211> LENGTH: 6
<212> TYPE: PRT
<213> ORGANISM: Rattus rattus

<400> SEQUENCE: 8

His Thr Gly Ser Gly Gly
1 5

<210> SEQ ID NO 9
<211> LENGTH: 351
<212> TYPE: PRT
<213> ORGANISM: Rattus rattus

<400> SEQUENCE: 9

Gln Asn Leu Phe Thr Lys Asp Val Thr Val Ile Glu Gly Glu Val Ala
1 5 10 15

Thr Ile Ser Cys Gln Val Asn Lys Ser Asp Asp Ser Val Ile Gln Leu
20 25 30

Leu Asn Pro Asn Arg Gln Thr Ile Tyr Phe Arg Asp Phe Arg Pro Leu
35 40 45

Lys Asp Ser Arg Phe Gln Leu Leu Asn Phe Ser Ser Ser Glu Leu Lys
50 55 60

Val Ser Leu Thr Asn Val Ser Ile Ser Asp Glu Gly Arg Tyr Phe Cys
65 70 75 80

Gln Leu Tyr Thr Asp Pro Pro Gln Glu Ser Tyr Thr Thr Ile Thr Val
85 90 95

Leu Val Pro Pro Arg Asn Leu Met Ile Asp Ile Gln Lys Asp Thr Ala
100 105 110

Val Glu Gly Glu Glu Ile Glu Val Asn Cys Thr Ala Met Ala Ser Lys
115 120 125

Pro Ala Thr Thr Ile Arg Trp Phe Lys Gly Asn Thr Glu Leu Lys Gly
130 135 140

Lys Ser Glu Val Glu Glu Trp Ser Asp Met Tyr Thr Val Thr Ser Gln
145 150 155 160

Leu Met Leu Lys Val His Lys Glu Asp Asp Gly Val Pro Val Ile Cys
165 170 175

Gln Val Glu His Pro Ala Val Thr Gly Asn Leu Gln Thr Gln Arg Tyr
180 185 190

Leu Glu Val Gln Tyr Lys Pro Gln Val His Ile Gln Met Thr Tyr Pro
195 200 205

Leu Gln Gly Leu Thr Arg Glu Gly Asp Ala Leu Glu Leu Thr Cys Glu
210 215 220

Ala Ile Gly Lys Pro Gln Pro Val Met Val Thr Trp Val Arg Val Asp
225 230 235 240

Asp Glu Met Pro Gln His Ala Val Leu Ser Gly Pro Asn Leu Phe Ile
245 250 255

Asn Asn Leu Asn Lys Thr Asp Asn Gly Thr Tyr Arg Cys Glu Ala Ser
260 265 270

Asn Ile Val Gly Lys Ala His Ser Asp Tyr Met Leu Tyr Val Tyr Asp
275 280 285

Pro Pro Thr Thr Ile Pro Pro Pro Thr Thr Thr Thr Thr Thr Thr Thr
290 295 300

Thr Thr Thr Thr Thr Ile Leu Thr Ile Ile Thr Asp Ser Arg Ala Gly
305 310 315 320

Glu Glu Gly Ser Ile Arg Ala Ala Ala Ala Glu Gln Lys Leu Ile Ser
325 330 335

Glu Glu Asp Leu Asn Ser Ala Val Asp His His His His His His
340 345 350

<210> SEQ ID NO 10
<211> LENGTH: 343
<212> TYPE: PRT
<213> ORGANISM: Rattus rattus

<400> SEQUENCE: 10

Gln Asn Leu Phe Thr Lys Asp Val Thr Val Ile Glu Gly Glu Val Ala
1 5 10 15

Thr Ile Ser Cys Gln Val Asn Lys Ser Asp Asp Ser Val Ile Gln Leu
20 25 30

Leu Asn Pro Asn Arg Gln Thr Ile Tyr Phe Arg Asp Phe Arg Pro Leu
35 40 45

Lys Asp Ser Arg Phe Gln Leu Leu Asn Phe Ser Ser Ser Glu Leu Lys
50 55 60

Val Ser Leu Thr Asn Val Ser Ile Ser Asp Glu Gly Arg Tyr Phe Cys
65 70 75 80

Gln Leu Tyr Thr Asp Pro Pro Gln Glu Ser Tyr Thr Thr Ile Thr Val
85 90 95

Leu Val Pro Pro Arg Asn Leu Met Ile Asp Ile Gln Lys Asp Thr Ala
100 105 110

Val Glu Gly Glu Glu Ile Glu Val Asn Cys Thr Ala Met Ala Ser Lys
115 120 125

Pro Ala Thr Thr Ile Arg Trp Phe Lys Gly Asn Thr Glu Leu Lys Gly
130 135 140

Lys Ser Glu Val Glu Glu Trp Ser Asp Met Tyr Thr Val Thr Ser Gln
145 150 155 160

Leu Met Leu Lys Val His Lys Glu Asp Asp Gly Val Pro Val Ile Cys
165 170 175

Gln Val Glu His Pro Ala Val Thr Gly Asn Leu Gln Thr Gln Arg Tyr
180 185 190

Leu Glu Val Gln Tyr Lys Pro Gln Val His Ile Gln Met Thr Tyr Pro
195 200 205

Leu Gln Gly Leu Thr Arg Glu Gly Asp Ala Leu Glu Leu Thr Cys Glu
210 215 220

Ala Ile Gly Lys Pro Gln Pro Val Met Val Thr Trp Val Arg Val Asp
225 230 235 240

Asp Glu Met Pro Gln His Ala Val Leu Ser Gly Pro Asn Leu Phe Ile
245 250 255

Asn Asn Leu Asn Lys Thr Asp Asn Gly Thr Tyr Arg Cys Glu Ser Asn
260 265 270

Ile Val Gly Lys Ala His Ser Asp Tyr Met Leu Tyr Val Tyr Asp Pro
275 280 285

Pro Thr Thr Ile Pro Pro Pro Thr Thr Thr Thr Thr Thr Thr Thr Thr
290 295 300

Thr Thr Thr Thr Ile Leu Thr Ile Ile Thr Asp Thr Thr Ala Thr Thr
305 310 315 320

Glu Pro Ala Val His Asp Ser Arg Ala Gly Glu Glu Gly Ser Ile Arg
325 330 335

Ala His His His His His His
340

<210> SEQ ID NO 11
<211> LENGTH: 590
<212> TYPE: PRT
<213> ORGANISM: Artificial Sequence
<220> FEATURE:
<223> OTHER INFORMATION: rat-human chimera

<400> SEQUENCE: 11

Asn Leu Phe Thr Lys Asp Val Thr Val Ile Glu Gly Glu Val Ala Thr
1 5 10 15

Ile Ser Cys Gln Val Asn Lys Ser Asp Asp Ser Val Ile Gln Leu Leu
20 25 30

Asn Pro Asn Arg Gln Thr Ile Tyr Phe Arg Asp Phe Arg Pro Leu Lys
35 40 45

Asp Ser Arg Phe Gln Leu Leu Asn Phe Ser Ser Ser Glu Leu Lys Val
50 55 60

Ser Leu Thr Asn Val Ser Ile Ser Asp Glu Gly Arg Tyr Phe Cys Gln
65 70 75 80

Leu Tyr Thr Asp Pro Pro Gln Glu Ser Tyr Thr Thr Ile Thr Val Leu
85 90 95

Val Pro Pro Arg Asn Leu Met Ile Asp Ile Gln Lys Asp Thr Ala Val
100 105 110

Glu Gly Glu Glu Ile Glu Val Asn Cys Thr Ala Met Ala Ser Lys Pro
115 120 125

Ala Thr Thr Ile Arg Trp Phe Lys Gly Asn Thr Glu Leu Lys Gly Lys
130 135 140

Ser Glu Val Glu Glu Trp Ser Asp Met Tyr Thr Val Thr Ser Gln Leu
145 150 155 160

Met Leu Lys Val His Lys Glu Asp Asp Gly Val Pro Val Ile Cys Gln
165 170 175

Val Glu His Pro Ala Val Thr Gly Asn Leu Gln Thr Gln Arg Tyr Leu
180 185 190

Glu Val Gln Tyr Lys Pro Gln Val His Ile Gln Met Thr Tyr Pro Leu
195 200 205

Gln Gly Leu Thr Arg Glu Gly Asp Ala Leu Glu Leu Thr Cys Glu Ala
210 215 220

Ile Gly Lys Pro Gln Pro Val Met Val Thr Trp Val Arg Val Asp Asp
225 230 235 240

Glu Met Pro Gln His Ala Val Leu Ser Gly Pro Asn Leu Phe Ile Asn
245 250 255

```
Asn Leu Asn Lys Thr Asp Asn Gly Thr Tyr Arg Cys Glu Ala Ser Asn
            260                 265                 270

Ile Val Gly Lys Ala His Ser Asp Tyr Met Leu Tyr Val Tyr Asp Pro
        275                 280                 285

Pro Thr Thr Ile Pro Pro Pro Thr Thr Thr Thr Thr Thr Thr Thr Thr
    290                 295                 300

Thr Thr Thr Thr Ile Leu Thr Ile Ile Thr Asp Thr Thr Ala Thr Thr
305                 310                 315                 320

Glu Pro Ala Val His Gly Leu Thr Gln Leu Pro Asn Ser Ala Glu Glu
                325                 330                 335

Leu Asp Ser Glu Asp Leu Ser Asp Ser Arg Ala Gly Glu Glu Gly Ser
            340                 345                 350

Ile Arg Ala Ala Ala Ala Glu Pro Lys Ser Cys Asp Lys Thr His Thr
        355                 360                 365

Cys Pro Pro Cys Pro Ala Pro Glu Leu Leu Gly Gly Pro Ser Val Phe
    370                 375                 380

Leu Phe Pro Pro Lys Pro Lys Asp Thr Leu Met Ile Ser Arg Thr Pro
385                 390                 395                 400

Glu Val Thr Cys Val Val Val Asp Val Ser His Glu Asp Pro Glu Val
                405                 410                 415

Lys Phe Asn Trp Tyr Val Asp Gly Val Glu Val His Asn Ala Lys Thr
            420                 425                 430

Lys Pro Arg Glu Glu Gln Tyr Asn Ser Thr Tyr Arg Val Val Ser Val
        435                 440                 445

Leu Thr Val Leu His Gln Asp Trp Leu Asn Gly Lys Glu Tyr Lys Cys
    450                 455                 460

Lys Val Ser Asn Lys Ala Leu Pro Ala Pro Ile Glu Lys Thr Ile Ser
465                 470                 475                 480

Lys Ala Lys Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
    530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590
```

<210> SEQ ID NO 12
<211> LENGTH: 573
<212> TYPE: PRT
<213> ORGANISM: Artificial Sequence
<220> FEATURE:
<223> OTHER INFORMATION: rat-human chimera

<400> SEQUENCE: 12

```
Gln Asn Leu Phe Thr Lys Asp Val Thr Val Ile Glu Gly Glu Val Ala
1               5                   10                  15

Thr Ile Ser Cys Gln Val Asn Lys Ser Asp Asp Ser Val Ile Gln Leu
            20                  25                  30
```

-continued

```
Leu Asn Pro Asn Arg Gln Thr Ile Tyr Phe Arg Asp Phe Arg Pro Leu
        35                  40                  45

Lys Asp Ser Arg Phe Gln Leu Leu Asn Phe Ser Ser Ser Glu Leu Lys
    50                  55                  60

Val Ser Leu Thr Asn Val Ser Ile Ser Asp Glu Gly Arg Tyr Phe Cys
65                  70                  75                  80

Gln Leu Tyr Thr Asp Pro Pro Gln Glu Ser Tyr Thr Thr Ile Thr Val
                85                  90                  95

Leu Val Pro Pro Arg Asn Leu Met Ile Asp Ile Gln Lys Asp Thr Ala
            100                 105                 110

Val Glu Gly Glu Glu Ile Glu Val Asn Cys Thr Ala Met Ala Ser Lys
        115                 120                 125

Pro Ala Thr Thr Ile Arg Trp Phe Lys Gly Asn Thr Glu Leu Lys Gly
    130                 135                 140

Lys Ser Glu Val Glu Glu Trp Ser Asp Met Tyr Thr Val Thr Ser Gln
145                 150                 155                 160

Leu Met Leu Lys Val His Lys Glu Asp Asp Gly Val Pro Val Ile Cys
                165                 170                 175

Gln Val Glu His Pro Ala Val Thr Gly Asn Leu Gln Thr Gln Arg Tyr
            180                 185                 190

Leu Glu Val Gln Tyr Lys Pro Gln Val His Ile Gln Met Thr Tyr Pro
        195                 200                 205

Leu Gln Gly Leu Thr Arg Glu Gly Asp Ala Leu Glu Leu Thr Cys Glu
    210                 215                 220

Ala Ile Gly Lys Pro Gln Pro Val Met Val Thr Trp Val Arg Val Asp
225                 230                 235                 240

Asp Glu Met Pro Gln His Ala Val Leu Ser Gly Pro Asn Leu Phe Ile
                245                 250                 255

Asn Asn Leu Asn Lys Thr Asp Asn Gly Thr Tyr Arg Cys Glu Ala Ser
            260                 265                 270

Asn Ile Val Gly Lys Ala His Ser Asp Tyr Met Leu Tyr Val Tyr Asp
        275                 280                 285

Pro Pro Thr Thr Ile Pro Pro Pro Thr Thr Thr Thr Thr Thr Thr Thr
    290                 295                 300

Thr Thr Thr Thr Thr Ile Leu Thr Ile Ile Thr Asp Thr Thr Ala Thr
305                 310                 315                 320

Thr Glu Pro Ala Val His Asp Ser Arg Ala Gly Glu Glu Gly Ser Ile
                325                 330                 335

Arg Ala Ala Ala Ala Glu Pro Lys Ser Cys Asp Lys Thr His Thr Cys
            340                 345                 350

Pro Pro Cys Pro Ala Pro Glu Leu Leu Gly Gly Pro Ser Val Phe Leu
        355                 360                 365

Phe Pro Pro Lys Pro Lys Asp Thr Leu Met Ile Ser Arg Thr Pro Glu
    370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
        435                 440                 445
```

Val Ser Asn Lys Ala Leu Pro Ala Pro Ile Glu Lys Thr Ile Ser Lys
450 455 460

Ala Lys Gly Gln Pro Arg Glu Pro Gln Val Tyr Thr Leu Pro Pro Ser
465 470 475 480

Arg Asp Glu Leu Thr Lys Asn Gln Val Ser Leu Thr Cys Leu Val Lys
485 490 495

Gly Phe Tyr Pro Ser Asp Ile Ala Val Glu Trp Glu Ser Asn Gly Gln
500 505 510

Pro Glu Asn Asn Tyr Lys Thr Thr Pro Pro Val Leu Asp Ser Asp Gly
515 520 525

Ser Phe Phe Leu Tyr Ser Lys Leu Thr Val Asp Lys Ser Arg Trp Gln
530 535 540

Gln Gly Asn Val Phe Ser Cys Ser Val Met His Glu Ala Leu His Asn
545 550 555 560

His Tyr Thr Gln Lys Ser Leu Ser Leu Ser Pro Gly Lys
565 570

<210> SEQ ID NO 13
<211> LENGTH: 475
<212> TYPE: PRT
<213> ORGANISM: Rattus rattus

<400> SEQUENCE: 13

Met Ile Ser Pro Pro Leu Asn Thr Met Thr Ile Thr Met Glu Trp Ser
1 5 10 15

Trp Val Phe Leu Phe Leu Leu Ser Val Thr Ala Gly Val His Ser Gln
20 25 30

Val Gln Leu Gln Gln Ser Gly Ala Glu Leu Ala Lys Pro Gly Ser Ser
35 40 45

Val Lys Ile Ser Cys Lys Ala Ser Gly Tyr Thr Phe Ser Asn Tyr Asp
50 55 60

Ile Ser Trp Ile Lys Gln Thr Thr Gly Gln Gly Leu Asp Tyr Ile Gly
65 70 75 80

Tyr Ile His Thr Gly Ser Gly Gly Thr Tyr Tyr Asn Glu Lys Phe Lys
85 90 95

Gly Lys Ala Thr Leu Thr Val Asp Lys Ser Ser Ser Thr Ala Phe Met
100 105 110

Gln Leu Ser Ser Leu Thr Pro Glu Asp Thr Ala Val Tyr Tyr Cys Ala
115 120 125

Arg Thr Pro Tyr Val Tyr Tyr Gly Ser Gly Tyr Phe Asp Phe Trp Gly
130 135 140

Pro Gly Thr Met Val Thr Val Ser Ser Ala Glu Thr Thr Ala Pro Ser
145 150 155 160

Val Tyr Pro Leu Ala Pro Gly Thr Ala Leu Lys Ser Asn Ser Met Val
165 170 175

Thr Leu Gly Cys Leu Val Lys Gly Tyr Phe Pro Glu Pro Val Thr Val
180 185 190

Thr Trp Asn Ser Gly Ala Leu Ser Ser Gly Val His Thr Phe Pro Ala
195 200 205

Val Leu Gln Ser Gly Leu Tyr Thr Leu Thr Ser Ser Val Thr Val Pro
210 215 220

Ser Ser Thr Trp Ser Ser Gln Ala Val Thr Cys Asn Val Ala His Pro
225 230 235 240

Ala Ser Ser Thr Lys Val Asp Lys Lys Ile Val Pro Arg Glu Cys Asn
245 250 255

```
Pro Cys Gly Cys Thr Gly Ser Glu Val Ser Ser Val Phe Ile Phe Pro
            260                 265                 270

Pro Lys Thr Lys Asp Val Leu Thr Ile Thr Leu Thr Pro Lys Val Thr
        275                 280                 285

Cys Val Val Val Asp Ile Ser Gln Asn Asp Pro Glu Val Arg Phe Ser
    290                 295                 300

Trp Phe Ile Asp Asp Val Glu Val His Thr Ala Gln Thr His Ala Pro
305                 310                 315                 320

Glu Lys Gln Ser Asn Ser Thr Leu Arg Ser Val Ser Glu Leu Pro Ile
                325                 330                 335

Val His Arg Asp Trp Leu Asn Gly Lys Thr Phe Lys Cys Lys Val Asn
            340                 345                 350

Ser Gly Ala Phe Pro Ala Pro Ile Glu Lys Ser Ile Ser Lys Pro Glu
        355                 360                 365

Gly Thr Pro Arg Gly Pro Gln Val Tyr Thr Met Ala Pro Pro Lys Glu
    370                 375                 380

Glu Met Thr Gln Ser Gln Val Ser Ile Thr Cys Met Val Lys Gly Phe
385                 390                 395                 400

Tyr Pro Pro Asp Ile Tyr Thr Glu Trp Lys Met Asn Gly Gln Pro Gln
                405                 410                 415

Glu Asn Tyr Lys Asn Thr Pro Pro Thr Met Asp Thr Asp Gly Ser Tyr
            420                 425                 430

Phe Leu Tyr Ser Lys Leu Asn Val Lys Lys Glu Thr Trp Gln Gln Gly
        435                 440                 445

Asn Thr Phe Thr Cys Ser Val Leu His Glu Gly Leu His Asn His His
    450                 455                 460

Thr Glu Lys Ser Leu Ser His Ser Pro Gly Lys
465                 470                 475


<210> SEQ ID NO 14
<211> LENGTH: 31
<212> TYPE: PRT
<213> ORGANISM: Rattus rattus

<400> SEQUENCE: 14

Met Ile Ser Pro Pro Leu Asn Thr Met Thr Ile Thr Met Glu Trp Ser
1               5                   10                  15

Trp Val Phe Leu Phe Leu Leu Ser Val Thr Ala Gly Val His Ser
            20                  25                  30


<210> SEQ ID NO 15
<211> LENGTH: 122
<212> TYPE: PRT
<213> ORGANISM: Rattus rattus

<400> SEQUENCE: 15

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Ser Asn Tyr
            20                  25                  30

Asp Ile Ser Trp Ile Lys Gln Thr Thr Gly Gln Gly Leu Asp Tyr Ile
        35                  40                  45

Gly Tyr Ile His Thr Gly Ser Gly Gly Thr Tyr Tyr Asn Glu Lys Phe
    50                  55                  60

Lys Gly Lys Ala Thr Leu Thr Val Asp Lys Ser Ser Ser Thr Ala Phe
65                  70                  75                  80
```

```
Met Gln Leu Ser Ser Leu Thr Pro Glu Asp Thr Ala Val Tyr Tyr Cys
                85                  90                  95

Ala Arg Thr Pro Tyr Val Tyr Tyr Gly Ser Gly Tyr Phe Asp Phe Trp
            100                 105                 110

Gly Pro Gly Thr Met Val Thr Val Ser Ser
        115                 120


<210> SEQ ID NO 16
<211> LENGTH: 322
<212> TYPE: PRT
<213> ORGANISM: Rattus rattus

<400> SEQUENCE: 16

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile Val Pro Arg Glu Cys Asn Pro Cys Gly Cys Thr Gly Ser Glu Val
            100                 105                 110

Ser Ser Val Phe Ile Phe Pro Pro Lys Thr Lys Asp Val Leu Thr Ile
        115                 120                 125

Thr Leu Thr Pro Lys Val Thr Cys Val Val Val Asp Ile Ser Gln Asn
    130                 135                 140

Asp Pro Glu Val Arg Phe Ser Trp Phe Ile Asp Asp Val Glu Val His
145                 150                 155                 160

Thr Ala Gln Thr His Ala Pro Glu Lys Gln Ser Asn Ser Thr Leu Arg
                165                 170                 175

Ser Val Ser Glu Leu Pro Ile Val His Arg Asp Trp Leu Asn Gly Lys
            180                 185                 190

Thr Phe Lys Cys Lys Val Asn Ser Gly Ala Phe Pro Ala Pro Ile Glu
        195                 200                 205

Lys Ser Ile Ser Lys Pro Glu Gly Thr Pro Arg Gly Pro Gln Val Tyr
    210                 215                 220

Thr Met Ala Pro Pro Lys Glu Glu Met Thr Gln Ser Gln Val Ser Ile
225                 230                 235                 240

Thr Cys Met Val Lys Gly Phe Tyr Pro Pro Asp Ile Tyr Thr Glu Trp
                245                 250                 255

Lys Met Asn Gly Gln Pro Gln Glu Asn Tyr Lys Asn Thr Pro Pro Thr
            260                 265                 270

Met Asp Thr Asp Gly Ser Tyr Phe Leu Tyr Ser Lys Leu Asn Val Lys
        275                 280                 285

Lys Glu Thr Trp Gln Gln Gly Asn Thr Phe Thr Cys Ser Val Leu His
    290                 295                 300

Glu Gly Leu His Asn His His Thr Glu Lys Ser Leu Ser His Ser Pro
305                 310                 315                 320

Gly Lys
```

<210> SEQ ID NO 17
<211> LENGTH: 240
<212> TYPE: PRT
<213> ORGANISM: Rattus rattus

<400> SEQUENCE: 17

```
Met Glu Ser Gln Thr Gln Val Leu Met Ser Leu Leu Leu Trp Ile Ser
1               5                   10                  15

Gly Thr Cys Gly Asp Ile Val Met Thr Gln Ser Pro Ser Ser Leu Ala
            20                  25                  30

Val Ser Ala Gly Glu Thr Val Thr Ile Asn Cys Lys Ser Ser Gln Ser
        35                  40                  45

Leu Leu Tyr Ser Gly Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Gln Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Ile Tyr
            100                 105                 110

Tyr Cys Gln Gln Tyr Tyr Asp Thr Pro Asp Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Met Glu Gln Leu Thr Ser Gly Gly Ala Thr Val Val Cys
145                 150                 155                 160

Phe Val Asn Asn Phe Tyr Pro Arg Asp Ile Ser Val Lys Trp Lys Ile
                165                 170                 175

Asp Gly Ser Glu Gln Arg Asp Gly Val Leu Asp Ser Val Thr Asp Gln
            180                 185                 190

Asp Ser Lys Asp Ser Thr Tyr Ser Met Ser Ser Thr Leu Ser Leu Thr
        195                 200                 205

Lys Val Glu Tyr Glu Arg His Asn Leu Tyr Thr Cys Glu Val Val His
    210                 215                 220

Lys Thr Ser Ser Ser Pro Val Val Lys Ser Phe Asn Arg Asn Glu Cys
225                 230                 235                 240
```

<210> SEQ ID NO 18
<211> LENGTH: 20
<212> TYPE: PRT
<213> ORGANISM: Rattus rattus

<400> SEQUENCE: 18

```
Met Glu Ser Gln Thr Gln Val Leu Met Ser Leu Leu Leu Trp Ile Ser
1               5                   10                  15

Gly Thr Cys Gly
            20
```

<210> SEQ ID NO 19
<211> LENGTH: 113
<212> TYPE: PRT
<213> ORGANISM: Rattus rattus

<400> SEQUENCE: 19

```
Asp Ile Val Met Thr Gln Ser Pro Ser Ser Leu Ala Val Ser Ala Gly
1               5                   10                  15
```

```
Glu Thr Val Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asp Thr Pro Asp Thr Phe Gly Ala Gly Thr Lys Leu Glu Leu
            100                 105                 110

Lys


<210> SEQ ID NO 20
<211> LENGTH: 107
<212> TYPE: PRT
<213> ORGANISM: Rattus rattus

<400> SEQUENCE: 20

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105


<210> SEQ ID NO 21
<211> LENGTH: 66
<212> TYPE: DNA
<213> ORGANISM: Artificial Sequence
<220> FEATURE:
<223> OTHER INFORMATION: Synthetic primer

<400> SEQUENCE: 21

gattacgcca agcttctaga tgaagtactc tttcttttct tcggagttgt tctgtcctcc     60

ttctgc                                                                66


<210> SEQ ID NO 22
<211> LENGTH: 41
<212> TYPE: DNA
<213> ORGANISM: Artificial Sequence
<220> FEATURE:
<223> OTHER INFORMATION: Synthetic primer

<400> SEQUENCE: 22

gattacgcca agcttatggc gagtgtagtg ctgccgagcg g                         41
```